(12) United States Patent
Dratz et al.

(10) Patent No.: US 7,582,260 B2
(45) Date of Patent: Sep. 1, 2009

(54) ZWITTERIONIC DYES FOR LABELING IN PROTEOMIC AND OTHER BIOLOGICAL ANALYSES

(75) Inventors: Edward A. Dratz, Bozeman, MT (US); Paul A. Grieco, Bozeman, MT (US)

(73) Assignee: Montana State University, Bozeman, MT (US)

( * ) Notice: Subject to any disclaimer, the term of this patent is extended or adjusted under 35 U.S.C. 154(b) by 737 days.

(21) Appl. No.: 10/761,818

(22) Filed: Jan. 20, 2004

(65) Prior Publication Data

US 2004/0248203 A1 Dec. 9, 2004

Related U.S. Application Data

(63) Continuation-in-part of application No. 10/623,447, filed on Jul. 18, 2003.

(60) Provisional application No. 60/396,950, filed on Jul. 18, 2002.

(51) Int. Cl.
G01N 21/00 (2006.01)
G01N 33/53 (2006.01)
G01N 33/00 (2006.01)
C12Q 1/68 (2006.01)
C07H 21/00 (2006.01)

(52) U.S. Cl. .................. 422/82.05; 435/6; 435/7.1; 536/25.32; 436/111

(58) Field of Classification Search .............. 436/86, 436/111; 435/6, 7.1; 536/25.32; 422/82.05
See application file for complete search history.

(56) References Cited

U.S. PATENT DOCUMENTS

| 4,774,339 | A | | 9/1988 | Haugland et al. | |
|---|---|---|---|---|---|
| 4,855,225 | A | * | 8/1989 | Fung et al. | 435/6 |
| 5,362,422 | A | * | 11/1994 | Masters | 510/424 |
| 5,936,087 | A | * | 8/1999 | Benson et al. | 546/33 |
| 6,051,719 | A | * | 4/2000 | Benson et al. | 548/416 |
| 6,972,326 | B2 | * | 12/2005 | Haugland et al. | 530/409 |
| 7,198,958 | B2 | * | 4/2007 | Meltola et al. | 436/546 |
| 2002/0160361 | A1 | * | 10/2002 | Loehrlein et al. | 435/6 |

FOREIGN PATENT DOCUMENTS

JP 2000029205 A * 1/2000

OTHER PUBLICATIONS

Panchuk-Voloshina et al., Alexa Dyes, a Series of New Fluorescent Dyes that Yield Exceptionally Bright, Photostable Conjugates, 1999, The Histochemical Society, Inc., vol. 47(9), p. 1179-1188.*

(Continued)

*Primary Examiner*—Jill Warden
*Assistant Examiner*—Lore Ramillano
(74) *Attorney, Agent, or Firm*—Cooley Godward Kronish, LLP

(57) ABSTRACT

The invention relates to compositions and methods useful in the labeling and identification of proteins. The invention provides for highly soluble zwitterionic dye molecules where the dyes and associated side groups are non-titratable and maintain their net zwitterionic character over a broad pH range, for example, between pH 3 and 12. These dye molecules find utility in a variety of applications, including use in the field of proteomics.

25 Claims, 16 Drawing Sheets

OTHER PUBLICATIONS

Berggren, K., et al., (2000) Background-free, high sensitivity staining of proteins in one- and two-dimensional sodium dodecyl sulfate-polyacrylamide gels using a luminescent ruthenium complex, *Electrophoresis* 21, 2509-2521.

Corthals, G. L., et al., (2000) The dynamic range of protein expression: a challenge for proteomic research, *Electrophoresis* 21: 1104-1115.

Database CAPLUS on STN, AN 2001:584663, Wang et al., Optical Recording Properties of a Novel Subphthalocyanine Thin Film:, Physica Status Solid A: Applied Research, 2001, vol. 186, No. 1, pp. 71-77, Abstract.

Gygi, S. P., et al., (1999) Quantitative analysis of complex protein mixtures using isotope-coded affinity tags, *Nat.Biotechnol.* 17: 994-999.

Gygi, S. P., et al., (2000) Evaluation of two-dimensional gel electrophoresis-based proteome analysis technology, *Proc.Natl. Acad.Sci.U.S.A* 97: 9390-9395.

Harry, J. L., et al., (2000) Proteomics: capacity versus utility, *Electrophoresis* 21: 1071-1081.

Haugland, R. P. and Kang, H. C. Chemically Reactive Dipyrromethene Boron Difluoride Dyes, *Molecular Probes, Inc.* 83, 458[4,774,339], 1-14, 1988.

Johnson, I. D., et al., (1991), Fluorescent membrane probes incorporating dipyrrometheneboron difluoride fluorophores, *Anal.Biochem* 198: 228-237.

Karolin, J., et al., (1994) Fluorescence and absorption spectroscopic properties of dipyrrometheneboron difluoride (BODIPY) derivatives in liquids, lipid membranes, and proteins, *J.Am.Chem.Soc.* 116: 7801-7806.

King et al., (1996) "Alkyl 2,2,2-Trifluorethanesulfonates (Tresylates): Elimination-Addition vs. Bimolecular Nucleophilic Substitution in Reactions with Nucleophiles in Aqueous Media" *J. Org. Chem.* 61, 7250-7255.

Mattew, J. B., et al., (1985) pH-dependent processes in proteins, *CRC Crit.Rev.Biochem* 18: 91-197.

McNamara P., et al., (2000) Fluorescent gel imaging with Typhoon 8600: *Life Science News*.

Patton, W. F. (2000) A thousand points of light: the application of fluorescence detection technologies to two-dimensional gel electrophoresis and proteomics *Electrophoresis* 21: 1123-1144.

Rabilloud, T., (2000) Detecting proteins separated by 2-D gel electrophoresis, *Anal.Chem.* 72: 48A-55A.

Tanford, C. (1962) The interpretation of hydrogen ion titration curves of proteins. *Adv.Protein Chem.* 17: 69-165.

Unlu, M., et al., (1997) Difference gel electrophoresis: a single gel method for detecting changes in protein extracts, *Electrophoresis* 18: 2071-2077.

Vos de Wael, E., et al., (1977) Pyromethene-BF2 complexes (4,4"-difluoro-4-bora-3a,4a-diaza-s-indacenes), Synthesis and luminescence properties, *Recl.Trav.Chim.Pays-Bas* 96: 306-309.

* cited by examiner

A

B

C

D

E

G

H

I

A3

B3

C3

D3

E3

F3

G3

H3

I3

U.S. 7,582,260 B2

ZWITTERIONIC DYES FOR LABELING IN PROTEOMIC AND OTHER BIOLOGICAL ANALYSES

This application is a continuation-in-part of U.S. patent application Ser. No. 10/623,447, filed Jul. 18, 2003 which claims the benefit of the priority date of U.S. Ser. No. 60/396, 950, filed Jul. 18, 2002, both of which are hereby expressly incorporated by reference.

GOVERNMENT INTERESTS

This research was supported by the US National Science Foundation Grant MCB 0139957 and US National Institutes of Health Grant R21RR16240.

FIELD OF THE INVENTION

The invention relates to compositions and methods useful in the labeling and identification of proteins. The invention provides for highly soluble zwitterionic dye molecules where the dyes and associated side groups are non-titratable and maintain their net zwitterionic character over a broad pH range, for example, between pH 3 and 12. These dye molecules find utility in a variety of applications, including use in the field of proteomics.

BACKGROUND OF THE INVENTION

Proteomics is the practice of identifying and quantifying the proteins, or the ratios of the amounts of proteins expressed in cells and tissues and their post-translational modifications, under different physiological conditions. Proteomics also encompasses the analysis of protein-protein interactions. Proteomics provides methods of studying the effect of biologically relevant variables on gene expression and protein production that provides advantages over genomic studies. While facile DNA chip methods have been rapidly developed and are widely available for analysis of mRNA levels, recent studies have shown little correlation between mRNA levels and levels of protein expression (Gygi, S. P., et al., (1999) Correlation between protein and mRNA abundance in yeast, *Mol Cell Biol.* 19, 1720-1730; Anderson, L., and Seilhamer, J. (1997) A comparison of selected mRNA and protein abundances in human liver, *Electrophoresis,* 18: 533-537). Furthermore, the functional state of a large fraction of proteins in cells is largely determined by post-translational modification, which must be analyzed directly at the protein level.

Proteomics can be performed using multiplex detection methods. Multiplex detection, or multiplexing, is defined as the transmission of two or more messages simultaneously with subsequent separation of the signals at the receiver. Multiplex fluorescence methods include, for example, multicolor fluorescence microscopy, multi-color fluorescent DNA sequencing, and two-color cDNA/mRNA expression array "chips". These techniques have been applied most commonly to the fields of cell biology and genomics. However multiplex fluorescence methods are also applicable to the field of proteomics. Current multiplex methods in use in the field of proteomics suffer from lack of detection sensitivity (U.S. Pat. No. 6,043,025; Amersham/Biosciences Operation Guide (2003) Ettan DIGE system; Beaumont, M., et al., (2001), Integrated technology platform for fluorescence 2-D difference gel electrophoresis, *Life Science News,* March 2001; Yan, J. X., et al., (2002) Fluorescence 2-D Difference Gel Electrophoresis and mass spectrometry based proteomic analysis of *Escherichia coli, Proteomics* 2: 1682-1698; Orange, P., et al., (2000), Fluorescence 2-D difference gel electrophoresis, *Life Science News* 5, 1-4; Patton W F, Beechem J M., (2002) Rainbow's end: the quest for multiplexed fluorescence quantitative analysis in proteomics, *Curr Opin Chem. Biol.* 6(1):63-9.

Predictions of cellular proteins from genome sequences indicate that two dimensional gel electrophoresis (2DE), with narrow isoelectric focusing pH ranges and cellular subfractionation, has the ability to resolve many, and sometimes essentially all, of the proteins in cells. However, the full potential protein detection potential of 2DE has not been realized primarily because of limitations in detection sensitivity and gel-to-gel reproducibility.

A major limitation of current proteomics techniques is the lack of compositions and methods that provide sufficient sensitivity to detect low levels of proteins. For example, proteins present at low copy number are difficult to detect using currently available methods that generally rely on the use of dyes to label proteins. In general, the dye molecules currently used in the art for detection of proteins during proteomic analysis possess a number of undesirable qualities. Notably, the presence of available dyes bound to the proteins before separation results in a substantial decrease in solubility of the proteins. This becomes especially problematic during the use of certain techniques used to separate the proteins, such as two-dimensional gel electrophoresis. Loss of protein solubility during the separation process results in loss of detectable proteins. With currently available techniques the lack of solubility increases as the number of dye molecules per protein molecule increases. Thus, one cannot counter the lack of dye sensitivity by adding more dye molecules to the protein. In addition, the addition of dyes can alter the isoelectric points (pIs) of the proteins, causing serious perturbations in the resolution of proteins using techniques such as 2DE, for example. Methods that relay on detecting proteins with dyes or other stains after separation suffer from lack of sensitivity, do not allow multiplex detection, and may have low dynamic range for detection, such as when using silver staining.

Other currently available proteomic techniques involve the use of biosynthetic isotopic labeling (Oda, Y., et al., (1999) Accurate quantitation of protein expression and site-specific phosphorylation, *Proc. Natl. Acad. Sci. U.S.A* 96: 6591-6596). This method is not readily applicable to animals or tissues and also requires mass spectral characterization of all the proteins separated, since expression differences are not apparent without analysis of the isotopic labels. Additional methods use predigestion of proteins into a large number of peptides before separation and derivatization of cysteine residues with isotope and affinity tags (Gygi, S. P., et al., (1999) Quantitative analysis of complex protein mixtures using isotope-coded affinity tags, *Nat. Biotechnol.* 17: 994-999.) or alternatively derivatization of N-terminal or lysine groups and isotope and/or affinity tags. Predigestion of proteins before separation produces a vast number of peptides that must be separated and analyzed for every experiment, a very demanding analytical process that is often hard to fully reproduce. The vast number of peptides that must be separated makes it extremely difficult to obtain high coverage of the protein sequences in the analysis, and if cysteine labeling is used only a small fraction of the peptides are analyzed. Thus it is very difficult to detect post-translational modifications in a general and reliable way using methods that require digestion of proteins into peptides before separation and analysis.

Thus a need exists for optical labeling molecules that possess enhanced properties of increased sensitivity and solubility to enhance detection sensitivity and recovery of intact proteins, to avoid perturbation of protein charge or isoelectric point, to allow versatile multiplex analysis of intact proteins for proteomics, so that intact proteins of interest can be selected more effectively and isolated for in depth analysis of post-translational protein modifications. In addition, there is a need for high sensitivity fluorescent covalent labeling dyes that are highly water soluble, that preserve the net charge of the labeled protein over a wide pH range for other applications that can benefit from the use of dye-labeled proteins.

SUMMARY OF THE INVENTION

In accordance with the objects outlined above, the present invention provides optical labeling molecules comprising at least one zwitterionic dye moiety, a titratable group moiety, and a functional linker moiety.

In a further aspect of the invention, the optical labeling molecule further comprises a cleavable moiety.

In a preferred embodiment of the invention, the charges on the zwitterionic dye moiety of the optical labeling molecule are independent of pH or non-titratable.

In one embodiment of the invention, the linker of the optical labeling molecule is an amine-reactive linker. In an additional embodiment of the invention, the linker is a thiol-reactive linker. The linker may be selected from the group consisting of imidoesters, N-hydroxysuccinimidyl esters, sulfhydryl-reactive maleimides, and iodoacetamides. Preferred linkers include, but are not limited to, succinimidyl groups, sulfosuccinimidyl groups, imido esters, isothiocyanates, aldehydes, sulfonylchlorides, arylating agents, maleimides, iodoacetamides, alkyl bromides, or benzoxidiazoles.

In yet a further aspect of the invention, the optical labeling molecule further comprises a second label. The second label can be, for example, a light stable isotope label or one or more heavy stable isotope labels.

In a preferred embodiment of the invention, the charges on the zwitterionic dye moiety of the optical labeling molecule are stable between pH 3-12.

In a preferred embodiment of the invention, the zwitterionic dye moiety of the optical labeling molecule comprises a BODIPY dye with at least one zwitterionic component.

The optical labeling molecule may have one of the following general structures:

T-ZD-A-; ZD-T-A-; ZD-T-C-A; T-ZD-C-A-; T-ZD-C-I-A-; or ZD-T-C-I-A-;

wherein ZD is a zwitterionic dye moiety, T is a titratable moiety, C is a cleavable moiety, I is a stable isotope moiety and A is a linker moiety.

A further aspect of invention provides for a target protein labeled with an optical labeling molecule of the invention, wherein the linker of the optical labeling molecule is covalently attached to the target protein.

In an additional aspect, the invention provides for a method of labeling a target protein comprising the steps of providing an optical labeling molecule comprising a zwitterionic dye moiety, a titratable group moiety, an optional cleavable moiety, and a functional linker moiety and contacting the target protein with the labeling molecule to form a labeled protein.

In yet a further aspect of the invention, a plurality of target proteins are each labeled with a different optical labeling molecule of the invention.

In an additional aspect, the invention provides for a method of performing protein analysis on a plurality of proteins comprising providing a plurality of different labeled proteins, each comprising a different zwitterionic dye moiety, a titratable group moiety, and an optional cleavable moiety, and determining the presence or absence of each of the different labeled proteins.

In yet a further aspect, the invention provides for the additional steps wherein the plurality of different labeled proteins are mixed and separated simultaneously prior to the determining the presence or absence of each of the different labeled proteins in the samples. The different labeled proteins may be separated by a method selected from the group consisting of 1D gel electrophoresis, 2D gel electrophoresis, gel electrophoresis, capillary electrophoresis, 1D chromatography, 2D chromatography, 3D chromatography, and the identities of the proteins identified by mass spectroscopy.

A further aspect of the invention provides for a method of protein analysis further comprising the step of determining the relative quantity of the different labeled proteins.

In yet a further aspect, the invention provides for a method of protein analysis wherein the cleavable moiety is present on the optical labeling molecule, the method further comprising cleaving the cleavable moiety to remove the labeling molecule from the different labeled proteins. In a further embodiment, the identities of the proteins separated by the above method and their post-translational modifications are determined by mass spectral techniques after removal of the dye tags.

An additional aspect of the invention provides for a method as described above wherein the cleavable moiety is present on the optical labeling molecule and each of the labeled proteins further comprise a different stable isotope tag moiety located between the functional linker moiety and the cleavable moiety. A further aspect provides for the additional steps of cleaving the cleavable moiety to produce isotope labeled proteins. A further aspect of the invention provides for the determination of the identity and post-translational modifications of the isotope labeled proteins by mass spectral techniques.

An additional aspect of the invention provides for a method of making the optical labeling molecules of the invention.

BRIEF DESCRIPTION OF THE DRAWINGS

In FIG. 4a, A=Ester activator, NHCH2CH2SH, or other linker; $R^1$ to $R^9$ to be defined; $R^{1, 1\ to\ p, 1\ to\ m}$ and $R^{2, 1\ to\ p, 1\ to\ m}$=to be defined; Ar=Aryl; r, n, m, p, q=0, 1, 2, 3 . . . For each value of p, there are p values of m. These p values can be equal or different. In FIG. 4B, A=Ester activator, NHCH2CH2SH, or other linker; CG=Cleavable group; $R^1$ to $R^9$=to be defined; $R^{1, 1\ to\ p, 1\ to\ m}$ and $R^{2, 1\ to\ p, 1\ to\ m}$=to be defined; Ar=Aryl; r, n, m, p, q=0, 1, 2, 3 . . . . For each value of p, there are p values of m. These p values can be equal or different. The dye depicted in FIG. 4B contains a cleavable group so that after separation of the dye-labeled proteins, the dyes can be removed to enhance enzymatic digestion of the target proteins and to simplify mass spectral or other analysis of the target proteins.

In FIG. 6A, n, m=1, 2, 3 . . . ; $R^{1\ to\ n, 1\ to\ m}$ and $R^{2, 1\ to\ n, 1\ to\ m}$=to be defined; A=nucleophilic attack activator. For each value of n, there are n values of m. These n values can be equal or different. In FIG. 6B, n, m=1, 2, 3 . . . ; $R^{1\ to\ n, 1\ to\ m}$ and $R^{2, 1\ to\ n\ 1\ to\ m}$=to be defined; CG=cleavable group; A=nucleophilic attack activator. For each value of p, there are p values of m. These p values can be equal or different. The dye depicted in FIG. 6B contains a cleavable group so that after separation of the dye-labeled proteins, the dyes can be removed to enhance enzymatic digestions and to simplify mass spectral or other analysis.

DETAILED DESCRIPTION OF THE INVENTION

Figure 1:
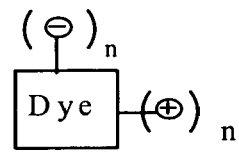
FIGS. 1A-1E depict a number of suitable schematic configurations for the addition of zwitterionic groups to dyes (1A, 1B and 1C) and dye derivatives (1D and 1E). A number of dye chromophores can be used and modified to embody the essential aspects of this invention
Figure 1:
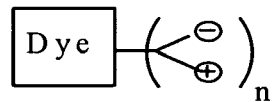
Figure 1:
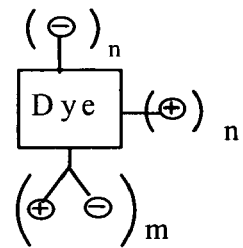
Figure 1:
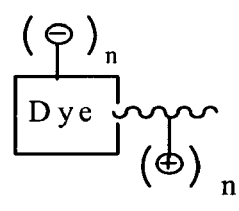
Figure 1:
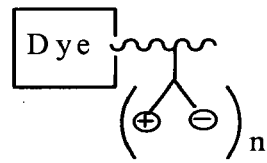
Figure 2:
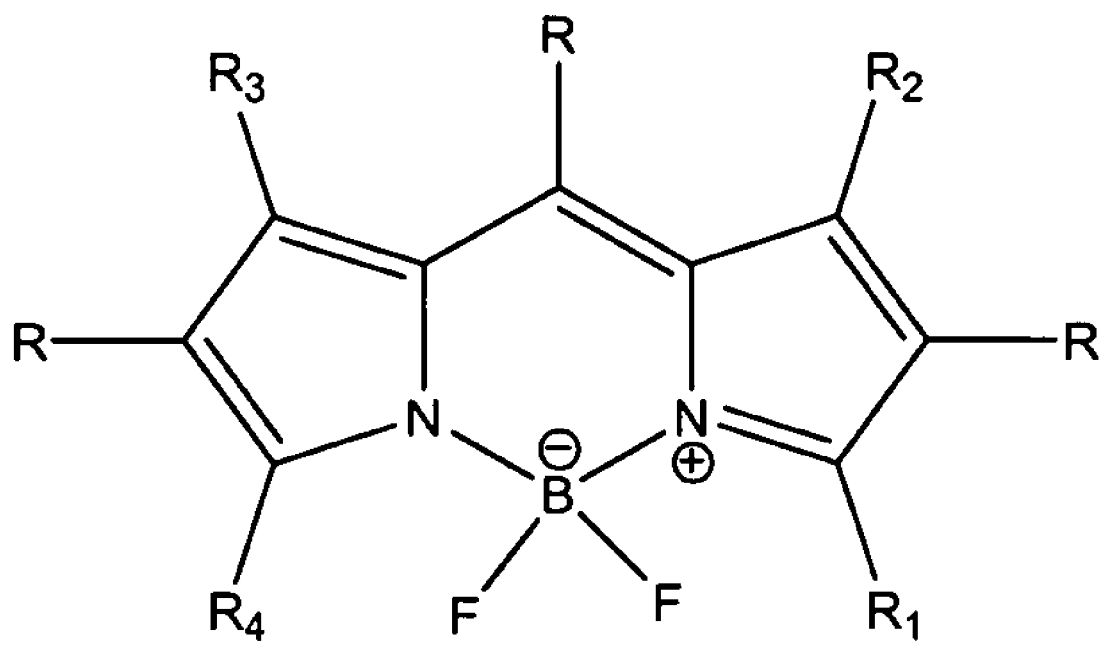
FIG. 2 depicts the general structure of the class of dyes known as BODIPY dyes. As described below, the R1 position frequently is used in this invention to add a derivative "tail" that may include a number of different "designer" chemical groups, the R2 and R3 positions can be used to add zwitterionic components, and the R4 position may be used to create other BODIPY type dyes with different colors. However, components can be added to different R groups as needed.
Figure 3:
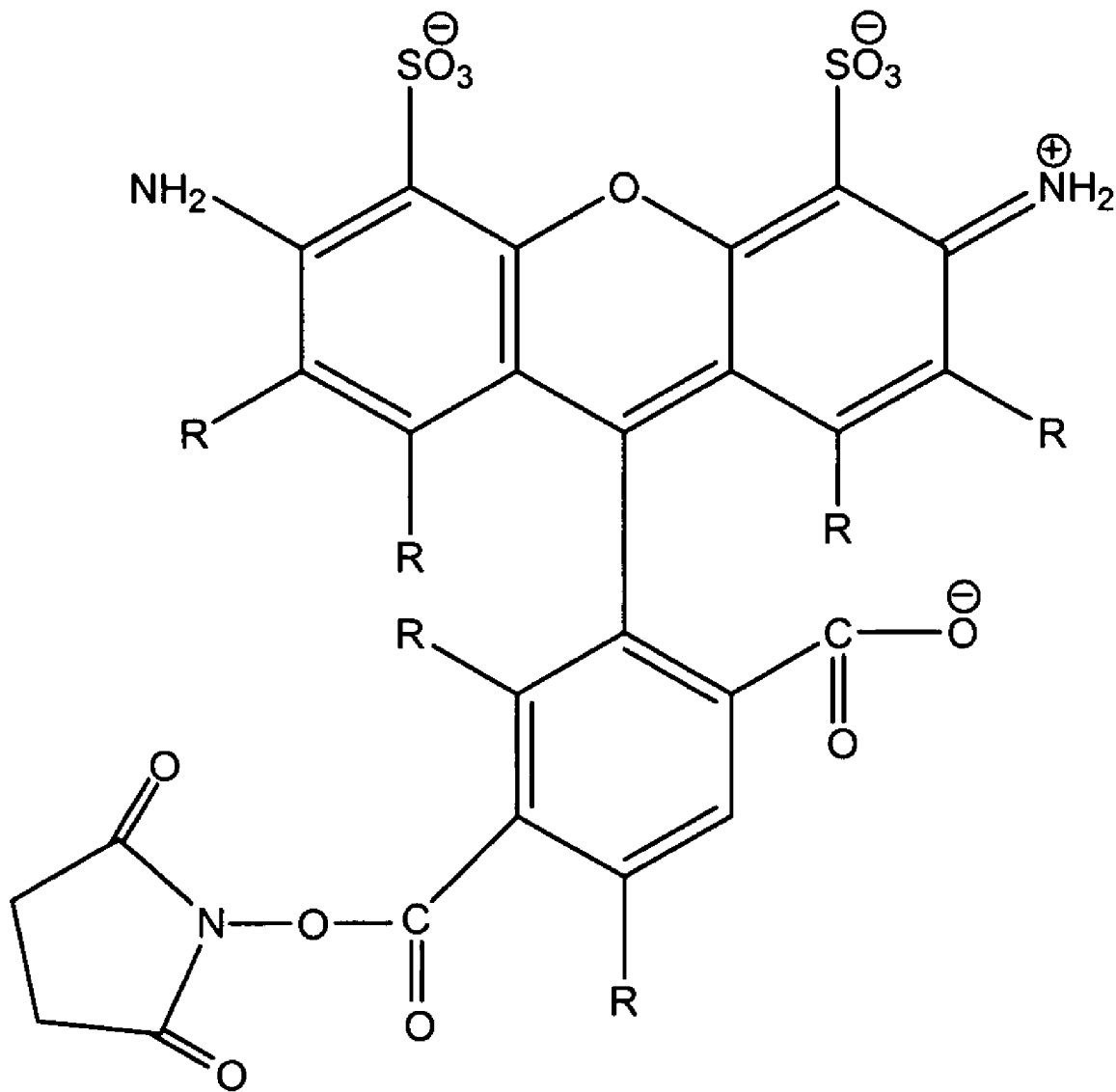
FIG. 3 depicts the general structure of an Alexa 488® (Molecular Probes) dye modified to change the molecular properties. Any of the R groups may be used to add nontitratable charged groups to balance out the charges on the dye to produce a zwitterionic charge balance, to add groups to replace the titration properties of the targets of the linkers on proteins, or to add "tails" for attachment of other components that may include cleavable groups and isotopic labeling groups to enhance the properties of the optical label. The reactive tail group shown may attach at the positions shown or may attach at one of the other R positions.
Figure 4A:
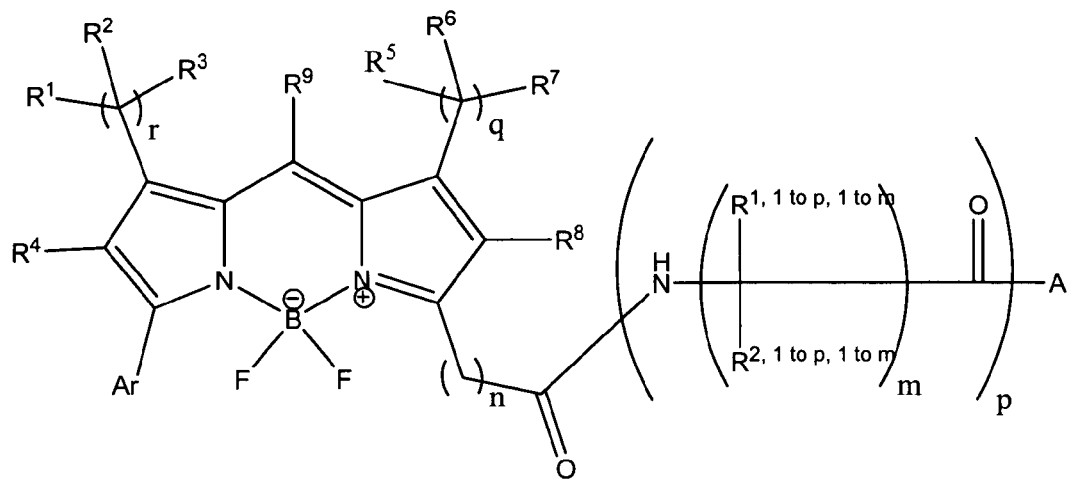
FIGS. 4A and 4B depicts the general structure of zwitterionic optical labeling molecules wherein the dye group is a BODIPY dye.
Figure 4B:
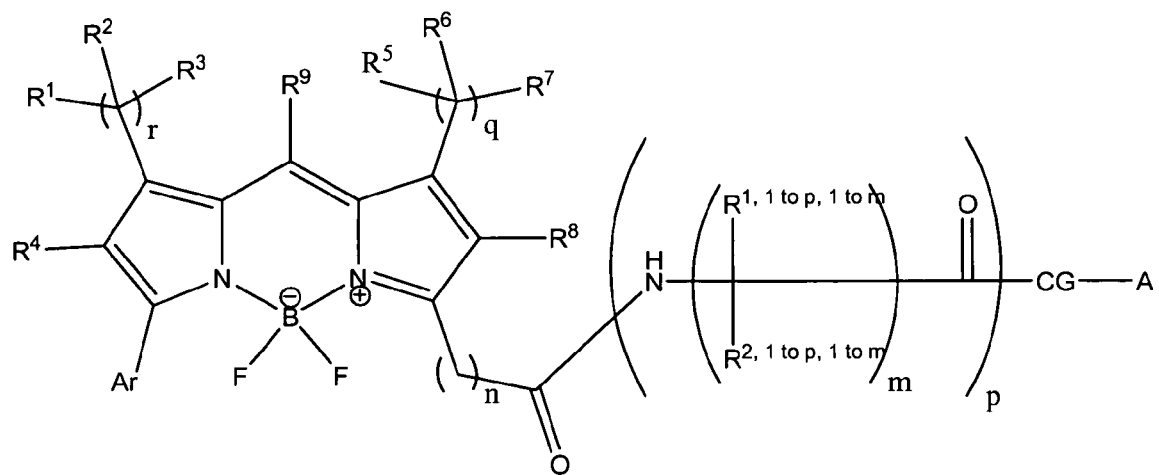
Figure 5:
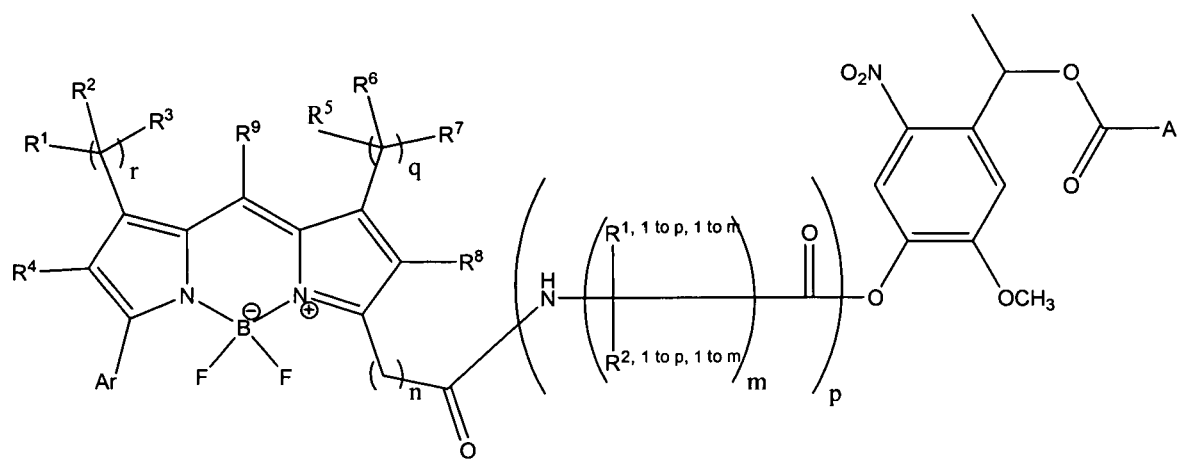
FIG. 5 depicts the general structure of a zwitterionic optical labeling molecule wherein the dye group is a BODIPY dye with a p-nitro anisole photo-cleavable group. A=Ester activator, NHCH2CH2SH, or other linker; $R^1$ to $R^9$=to be defined; $R^{1, 1\ to\ p, 1\ to\ m}$ and $R^{2, 1\ to\ p, 1\ to\ m}$=to be defined; Ar=Aryl; r, n, m, p, q=0, 1, 2, 3 . . . . For each value of p, there are p values of m. These p values can be equal or different.
Figure 6A:
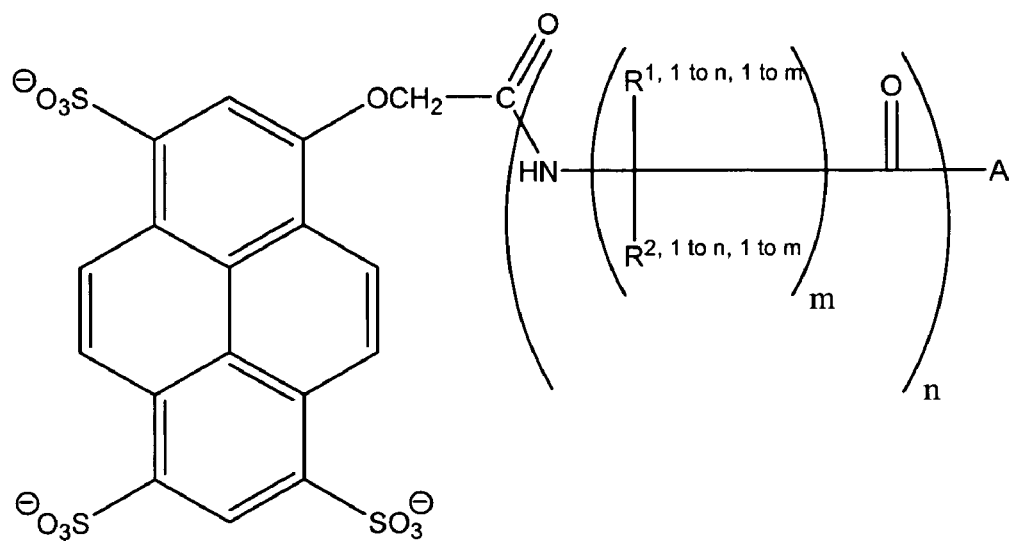
FIGS. 6A and 6B depicts two examples of a zwitterionic optical labeling molecule wherein the dye group is Cascade Blue dye.
Figure 6B:
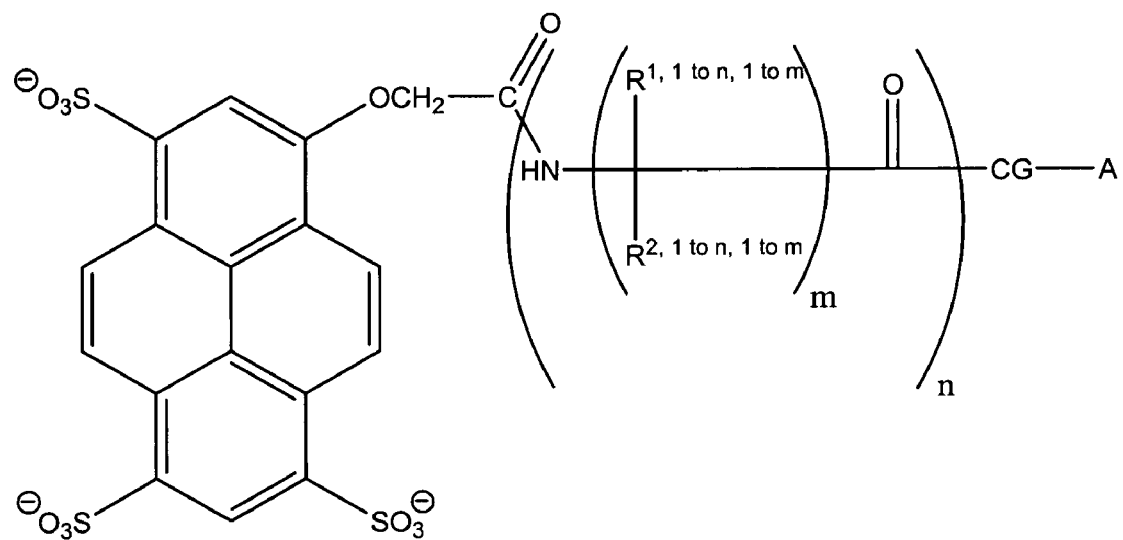

The present invention is directed toward compositions and methods useful in the optical labeling and detection of proteins. One aspect of the invention encompasses the use of the optical labeling molecule in the field of proteomics. As known in the art, one of the central problems with current proteomics methods is limited detection sensitivity. The best current post-labeling methods that are applied after protein separation (such as silver stains or fluorescent dyes) can detect low nanogram levels of protein per gel spot (Rabilloud, T., (2000) Detecting proteins separated by 2-D gel electrophoresis, *Anal. Chem.* 72: 48A-55A.; Berggren, K., et al., (2000) Background-free, high sensitivity staining of proteins in one- and two-dimensional sodium dodecyl sulfate-polyacrylamide gels using a luminescent ruthenium complex, *Electrophoresis* 21, 2509-2521), even with sophisticated laser scanners (McNamara P., et al., (2000) Fluorescent gel imaging with Typhoon 8600: *Life Science News*). This corresponds to detecting proteins in the range of about 300-3000 copies per cell under typical experimental conditions (Corthals, G. L., et al., (2000) The dynamic range of protein expression: a challenge for proteomic research, *Electrophoresis* 21: 1104-1115; Patton, W. F. (2000) A thousand points of light: the application of fluorescence detection technologies to two-dimensional gel electrophoresis and proteomics, *Electrophoresis* 21: 1123-1144), which falls short of the sensitivity needed to detect low abundance proteins such as regulatory proteins, that are often present in low copy number (Corthals, G. L., et al., (2000), *Electrophoresis* 21, 1104-1115; Gygi, S. P., et al., (2000) Evaluation of two-dimensional gel electrophoresis-based proteome analysis technology, *Proc. Natl. Acad. Sci. U.S.A* 97: 9390-9395; Harry, J. L., et al., (2000) Proteomics: capacity versus utility, *Electrophoresis* 21: 1071-1081). Pre-labeling proteins with fluorescent dyes can maximize the sensitivity by reducing the dye background after separation and by allowing the attachment of one or more dyes per protein. Currently available dyes, however, suffer from several shortcomings. For example, the available dyes typically adversely affect the solubility of the proteins to which they are attached. For example, a prior report, using prelabeling with fluorescent cyanine-based dyes (Cy) and multiplex detection (Unlu, M., et al., (1997) Difference gel electrophoresis: a single gel method for detecting changes in protein extracts, *Electrophoresis* 18: 2071-2077) required a very low multiplicity of dye labeling (0.01-0.02 dyes/protein) to minimize dye-induced reduction in protein solubility and dye-induced mobility shifts, and this severely limited the sensitivity attainable.

Accordingly, the present invention provides for optical labeling molecules that have enhanced properties for increased aqueous solubility over a wide pH range and enhanced detection sensitivity. Preferred optical labeling molecules of the invention are designed to contain zwitterionic groups which are designed to maintain their charges over a wide pH range to increase the solubility of proteins labeled with the optical labeling molecules in both aqueous and mixed polar solvents while minimizing pI shifts due to labeling, thereby facilitating separation and identification of the labeled proteins. In a preferred embodiment, the optical labeling molecule comprises a zwitterionic dye moiety, a titratable group moiety to replace the acid-base behavior of the target group on proteins used for linkage and a functional linker. In a further preferred embodiment, there is more than one zwitterionic group present on the zwitterionic dye moiety to further enhance the solubility of the zwitterionic dyes and the zwitterionic dye-labeled proteins over a wide pH range. The present invention in addition provides for many channels of multiplex protein detection in a single experiment, by using a family of detection dyes to label proteins from different biological treatments and thus overcomes problems with experimental reproducibility of the separations of the myriad of proteins present in cells, organelles and in tissues.

By "optical labeling molecule" is meant any molecule useful in covalently labeling biological molecules that permits the labeled molecule to be detected using methods that detect emission of an optical signal. Optical signals include, but are not limited to color, absorbance, luminescence, fluorescence, phosphorescence, with fluorescence usually being preferred for maximum detection sensitivity. That portion of the optical labeling molecule responsible for emission of the detectable signal is referred to as the chromophore of the dye moiety.

In a preferred embodiment of the invention, the optical labeling molecule is detected through measuring fluorescent emission. Fluorescent emission is luminescence that is caused by the absorption of radiation at one wavelength or a band of wavelengths in its absorption band (referred to as the excitation wavelength) followed by nearly immediate reradiation, largely at a different wavelength (referred to as the emission wavelength or the emission band).

In a preferred embodiment, the optical labeling moiety comprises a fluorescent dye. Suitable fluorophores include but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals"), pyrene, Malacite green, stilbene, Lucifer Yellow, Cascade Blue®, Texas Red, Cy dyes (Cy2, Cy3, Cy5, Cy5.5, Cy7, etc.), alexa dyes (including, but not limited to, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700 and Alexa Fluor 750, see Molecular Probes catalog, 9th Edition), phycoerythin, BODIPY dyes and derivatives, and others described in the 9th Edition of the Molecular Probes Handbook by Richard P. Haugland, hereby expressly incorporated by reference in its entirety. See also U.S. Pat. Nos. 6,130,101, 6,162,931, 6,291,203, all of which are hereby expressly incorporated by reference in their entirety, which depict suitable dye moieties. The figures depict a number of suitable dye moieties for use in the invention. Additionally, it is to be understood that the invention can be adapted by one of skill in the art to incorporate additional existing dye chromophores or new dye chromophores A variety of preferred dyes are depicted in the figures.

In a preferred embodiment, the optical labeling molecule comprises a zwitterionic dye moiety, a titratable group moiety and a functional linker. Zwitterionic groups are those that contain both positive and negative charges and are net neutral, but highly charged. By "zwitterionic dye moiety" is meant a dye that is designed to contain one or more zwitterionic groups, generally added as "zwitterionic components", e.g. separate positive and negative charged groups. The preferred zwitterionic dye moiety is non-titratable and thus maintains its zwitterionic charge character over a wide pH range (e.g. 3-12), with from pH 4-10 and pH 5-9 and pH 6-11 being useful as well.

In a preferred embodiment, the dye moiety, preferably a fluorophore, is derivatized to include side chain groups and/or a "tail" for the addition of components of zwitterionic charge pairs. As is shown in the Figures, any number of dyes can be derivatized to allow the addition both of components to produce a zwitterionic charge balance and the other components appropriate for the application (e.g. titratable groups, isotopes, linkers, etc.) of the optical labeling molecules of the invention.

In a preferred embodiment, the fluorophore is derivatized with an alkyl or polypeptide moiety that serves as a "tail" which include components of zwitterionic charge pairs and a functional group for the attachment of the other components of the labeling molecule. Preferred embodiments include alkyl chains, including substituted heteroalkyl chains, and alkylaryl groups, including alkyl groups interrupted with aryl groups, or a polypeptide chain framework, as are generally depicted in the figures.

As depicted in the figures, many of the positions of the fluorophores can be substituted with substituent chemical groups, generally termed "R" groups herein, for a variety of purposes, as outlined herein.

In a preferred embodiment, as will be appreciated by those in the art, a wide variety of possible R substituent groups may be used. Suitable R substitution groups, for the structures of the invention, include, but are not limited to, hydrogen, alkyl groups including substituted alkyl groups and heteroalkyl groups as defined below, aryl groups including substituted aryl and heteroaryl groups as defined below, sulfur moieties, amine groups, oxo groups, carbonyl groups, halogens, nitro groups, imino groups, alcohol groups, alkyoxy groups, amido groups, phosphorus moieties, ethylene glycols, ketones, aldehydes, esters, ethers, etc.

In addition, R groups on adjacent carbons, or adjacent R groups, can be attached to form cycloalkyl or cycloaryl groups, including heterocycloalkyl and heterocycloaryl groups together with the carbon atoms of the dye. These ring structures may be similarly substituted at any position with R groups.

In addition, as will be appreciated by those skilled in the art, each position designated above may have two R groups attached (R' and R"), depending on the valency of the position, although in a preferred embodiment only a single non-hydrogen R group is attached at any particular position; that is, preferably at least one of the R groups at each position is hydrogen. Thus, if R is an alkyl or aryl group, there is generally an additional hydrogen attached to the carbon, although not depicted herein.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with a preferred embodiment utilizing from about 1 to about 20 carbon atoms (C1-C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above. A peptide backbone can also be used to construct the "tail" moiety which includes zwitterionic charge balancing components and the other components of the labeling molecule.

A preferred heteroalkyl group is an alkyl amine. By "alkyl amine" or grammatical equivalents herein is meant an alkyl group as defined above, substituted with an amine group at any position. In addition, the alkyl amine may have other substitution groups, as outlined above for alkyl group. The amine may be primary (—NH$_2$R), secondary (—NHRR'), or tertiary (—NRR'R"). When the amine is a secondary or tertiary amine, preferred R groups are alkyl groups as defined above. A preferred alkyl amine is p-aminobenzyl. When the alkyl amine serves as the coordination site barrier, as described below, preferred embodiments utilize the nitrogen atom of the amine as a coordination atom, for example when the alkyl amine includes a pyridine or pyrrole ring.

By "aryl group" or "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc. As for alkyl groups, the aryl group may be substituted with a substitution group, generally depicted herein as R.

By "amino groups" or grammatical equivalents herein is meant —$NH_2$ (amine groups), —NHR and —$NR_2$ groups, with R being as defined herein. Preferred amines are tertiary (R—NR'R") or quaternary (R—NR'R"R'"+). Preferred R groups are alkyl groups as defined herein. By "nitro group" herein is meant an —$NO_2$ group.

By "sulfur containing moieties" herein is meant compounds containing sulfur atoms, including but not limited to, thia-, thio- and sulfo-compounds (including sulfoxides (—SO—), sulfones (—$SO_2$—), sulfonates (—$SO_3^-$), sulfates (—$OSO_3^-$), sulfides (RSR)), thiols (—SH), and disulfides (RSSR)). By "phosphorus containing moieties" herein is meant compounds containing phosphorus, including, but not limited to, phosphines, phosphites and phosphates. A preferred phosphorous moiety is the —PO(OH)(R)$_2$ group. The phosphorus may be an alkyl phosphorus; for example, DOTEP utilizes ethylphosphorus as a substitution group on DOTA. A preferred embodiment has a —PO(OH)$_2$R$_{25}$ group, with R$_{25}$ being a substitution group as outlined herein.

By "silicon containing moieties" herein is meant compounds containing silicon.

By "ketone" herein is meant an —RCOR— group.
By "aldehyde" herein is meant an —RCOH group.
By "ether" herein is meant an —R—O—R group.
By "alkyoxy group" herein is meant an —OR group.
By "ester" herein is meant a —COOR group.
By "halogen" herein is meant bromine, iodine, chlorine, or fluorine. Preferred substituted alkyls are partially or fully halogenated alkyls such as $CF_3$, etc.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —(O—$CH_2$—$CH_2$)$_r$— group, although each carbon atom of the ethylene group may also be singly or doubly substituted, i.e.—(O—$CR_2$—$CR_2$)$_n$—, with R as described above. Ethylene glycol derivatives with other heteroatoms in place of oxygen (i.e.—(N—$CH_2$—$CH_2$)$_n$— or —(S—$CH_2$—$CH_2$)$_n$—, or with substitution groups) are also preferred.

The optical labeling molecules, or other molecules defined herein, may contain one or more chiral centers and/or double bonds and therefore may exist as stereoisomers, such as double-bond isomers (i.e., geometric isomers), rotamers, enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. In general, as is depicted in the figures, charged groups are added to the zwitterionic dye moiety. In general, pairs of positive and negative charged moieties ("the zwitterionic components") are added at separate locations to the dye moiety (see for example FIG. 1A), although in some embodiments, both the positive and negative charges are added as single "branched" moieties (see FIG. 1B), or combinations thereof (see FIG. 1C). In some embodiments the chromophoric framework of the dye includes positively or negatively charged groups or includes some combination of positive and negative charges and suitable charge groups added to make the number of positive and negative groups equal (in order to form zwitterionic pairs). In some embodiments, the actual fluorophore has a derivative "tail", used as a linker to the other components of the optical labeling moiety, which can contain zwitterionic components as well (see FIGS. 1D and 1E). It should be noted that for purposes of the invention, these derivatives are included in the definition of "dye moiety". In additional embodiments, the zwitterionic components are added anywhere within the optical labeling moiety; for example, negative charges can be added to the fluorophore, and positive charges to the linker moiety, or vice versa.

Particularly preferred zwitterionic components are small alkyl groups (C2-C3) with quaternary ammonium groups (—NR3+), guanidine groups, or other positively charged groups which are not titratable until the edge of the most basic regions of interest, and negatively charged alkyl sulfonate or alkyl sulfate groups. Any other charged groups that are not titratable between pH 3-12 and are stable under aqueous conditions are suitable to include as components of zwitterionic groups.

Figure 8A:
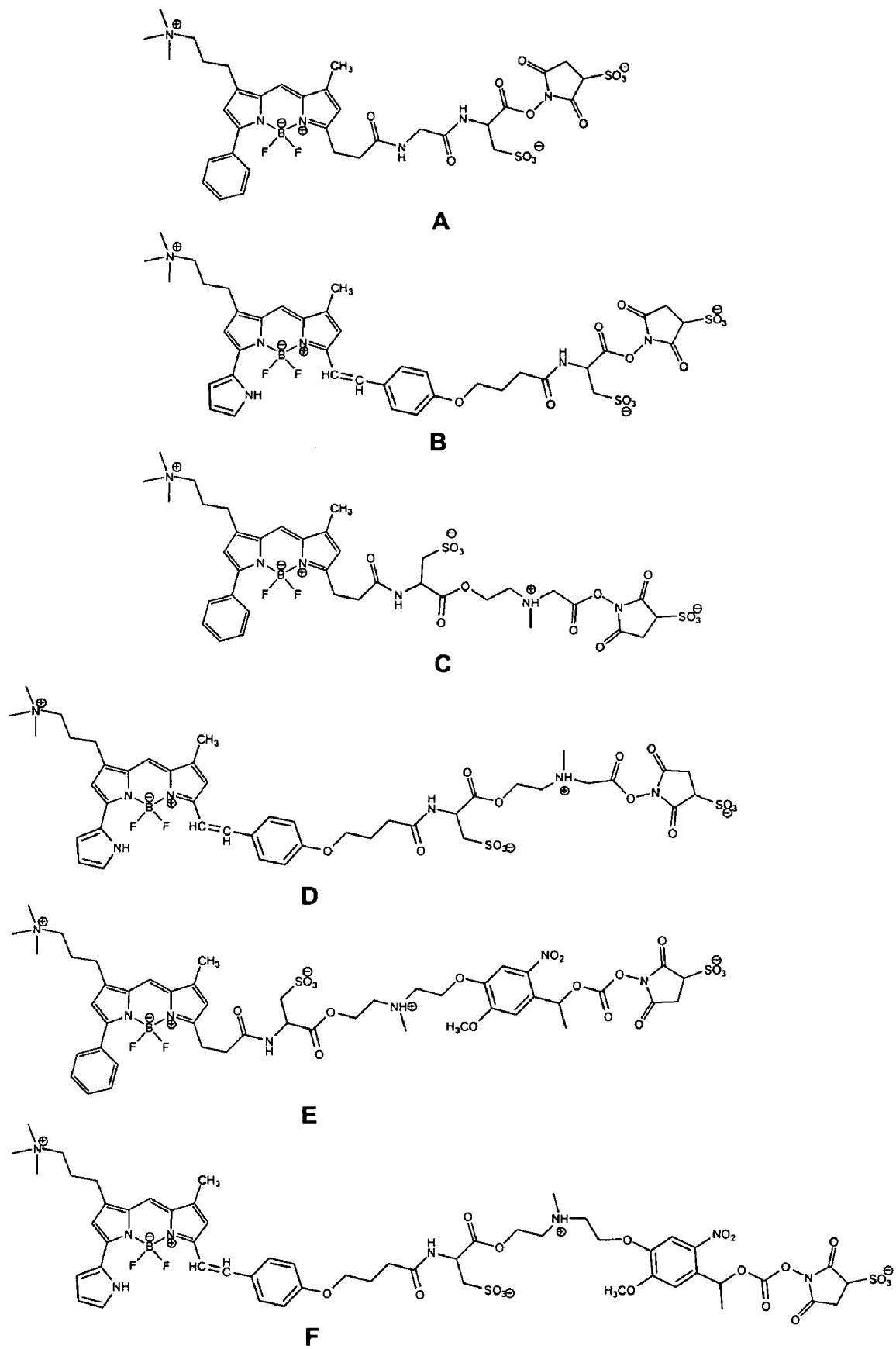
FIGS. 8A and 8B depicts the structures of zwitterionic dyes A-I.
Figure 8B:
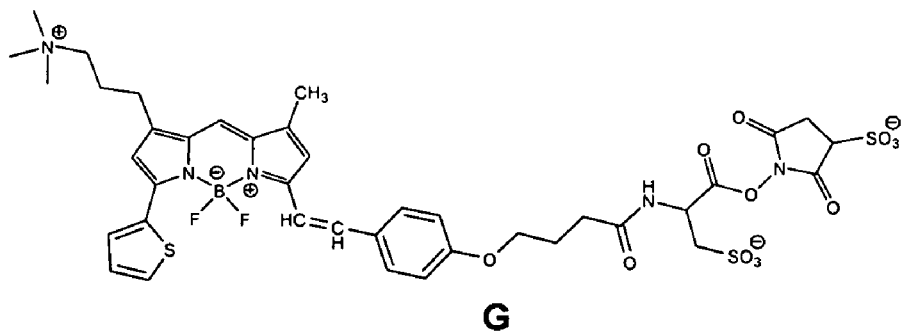
Figure 8B:
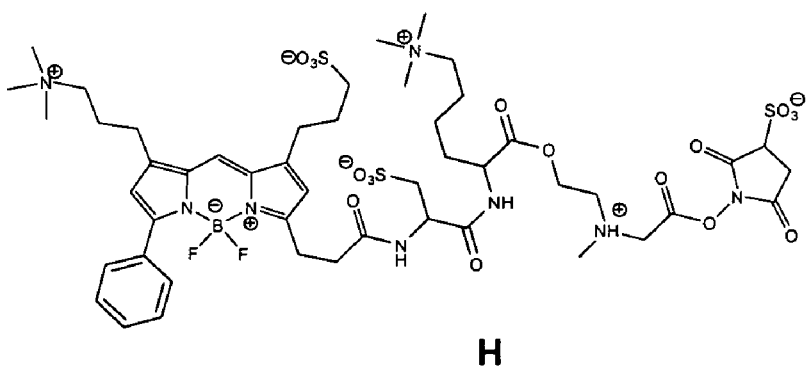
Figure 8B:
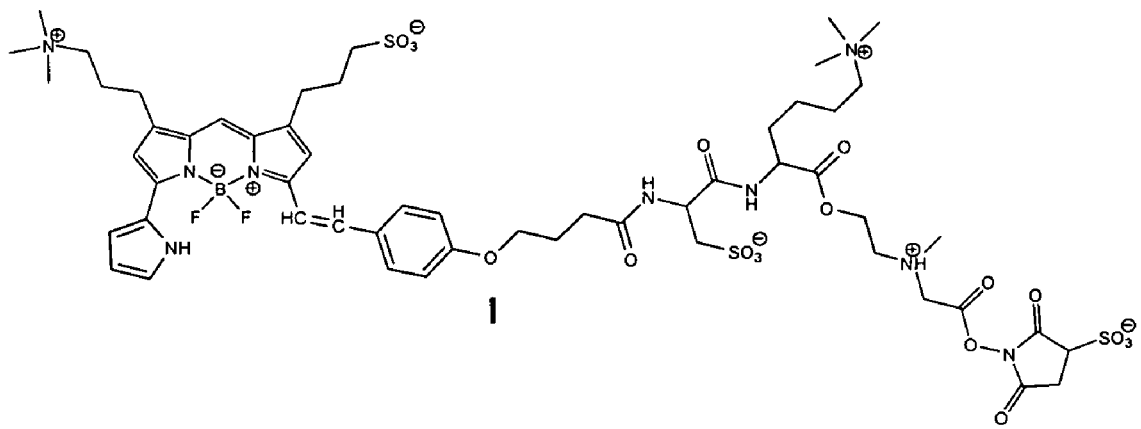

In a further preferred embodiment, the zwitterionic substitution of one, two or more quaternary ammonium group and one, two or more sulfonate groups are added to one of the family of boron difluoride diaza-indacene-propionic acid (BODIPY) dyes. The BODIPY family of dyes are stable molecules that have dyes have many favorable properties for use as the neutral dye moiety (Johnson, I. D., et al., (1991), Fluorescent membrane probes incorporating dipyrrometheneboron difluoride fluorophores, *Anal. Biochem* 198: 228-237; Karolin, J., et al., (1994) Fluorescence and absorption spectroscopic properties of dipyrrometheneboron difluoride (BODIPY) derivatives in liquids, lipid membranes, and proteins, *J. Am. Chem. Soc.* 116: 7801-7806, each of which are hereby incorporated by reference). BODIPY dyes have high sensitivity (extinction coefficient >70,000 cm$^{-1}$M$^{-1}$ and quantum yield 0.5-1.0), their fluorescence signals are insensitive to solvent and pH, and they exhibit high chemical and photo stability (Vos de Wael, E., et al., (1977) Pyromethene-BF2 complexes (4,4"-difluoro-4-bora-3a,4a-diaza-s-indacenes), Synthesis and luminescence properties, *Recl. Trav. Chim. Pays-Bas* 96: 306-309; Haugland, R. P. and Kang, H. C. Chemically Reactive DipyrrometheneBoron Difluoride Dyes, *Molecular Probes, Inc.* 83,458[4,774,339], 1-14.1988, each of which are hereby incorporated by reference). BODIPY dyes have narrow excitation spectra and a wide range of excitation/emission spectra are available in the different members of the series (9th Edition of the Molecular Probes Handbook, hereby expressly incorporated by reference), which facilitates the design and implementation of the multiplex protein detection techniques of this invention. Members of the BODIPY family of dyes have very similar structures but have different excitation and emission spectra that allows multiplex detection of proteins from two or more protein sample mixtures simultaneously on the same gel. Multiplex detection, or multiplexing, is defined as the transmission of two or more messages simultaneously with subsequent separation of the signals at the receiver. Specific examples of BODIPY dyes that have been engineered to contain one zwitterionic group are shown in FIGS. 8A and 8B as dyes A-G, in FIGS. 9A and 9B as dyes A2-G2, and in FIGS. 10A and 10B as dyes A3-G3.

In another preferred embodiment, a double zwitterionic substitution of two quaternary ammonium and two sulfonate groups are added to a neutral dye moiety. In a further preferred embodiment, the double zwitterionic substitution of two quaternary ammonium and sulfonate groups are added to a BODIPY dye moiety. Specific examples of BODIPY dyes that have been engineered to contain two zwitterionic groups are shown in FIG. 8B as dyes H and I, in FIG. 9B as dyes H2 and I2 and in FIG. 10B as dyes H3 and I3.

In general, dyes A, C, E and H (including the dyes designated A2, A3, C2, C3, E2, E3 and H2, H3) have an excitation/emission spectra of 528/547 nm and are efficiently excited by 488 or 532 nm lasers. Dyes B, D F and I (including the dyes designated B2, B3, D2, D3, F2, F3, I2 and I3) have an excitation/emission spectra of 630/650 nm and are efficiently excited by 633 nm lasers. Dye G (including the dyes designated G2, G3) has an excitation/emission spectra of 588/616 nm and is efficiently excited by 532 nm lasers. However, these numbers may vary slightly. Dyes from the first two groups, for example dye A and dye B, have exceedingly low optical "cross-talk" when excited at 488 or 633 nm, respectively, so that the excitation and emission of each group does not excite the other group and the signals from the two groups are well separated.

The spectra of dye G fits sufficiently well between the other two groups of dyes that three-color experiments can be done with 488, 532 and 633 nm lasers combined with suitable optical filters to differentiate the emission of the dyes. Measuring full emission spectra from spots on 2D gels will allow the effective separation of the signals from dyes that have strongly overlapping emission spectra and allow the simultaneous use of many similar dyes with slightly different spectra to carry out efficient multiplex detection of proteins with a much larger different numbers of color channels. The compounds of the invention are particularly suited for such use.

Example 1 describes a route of synthesis for dyes A-I.

Figure 9A:
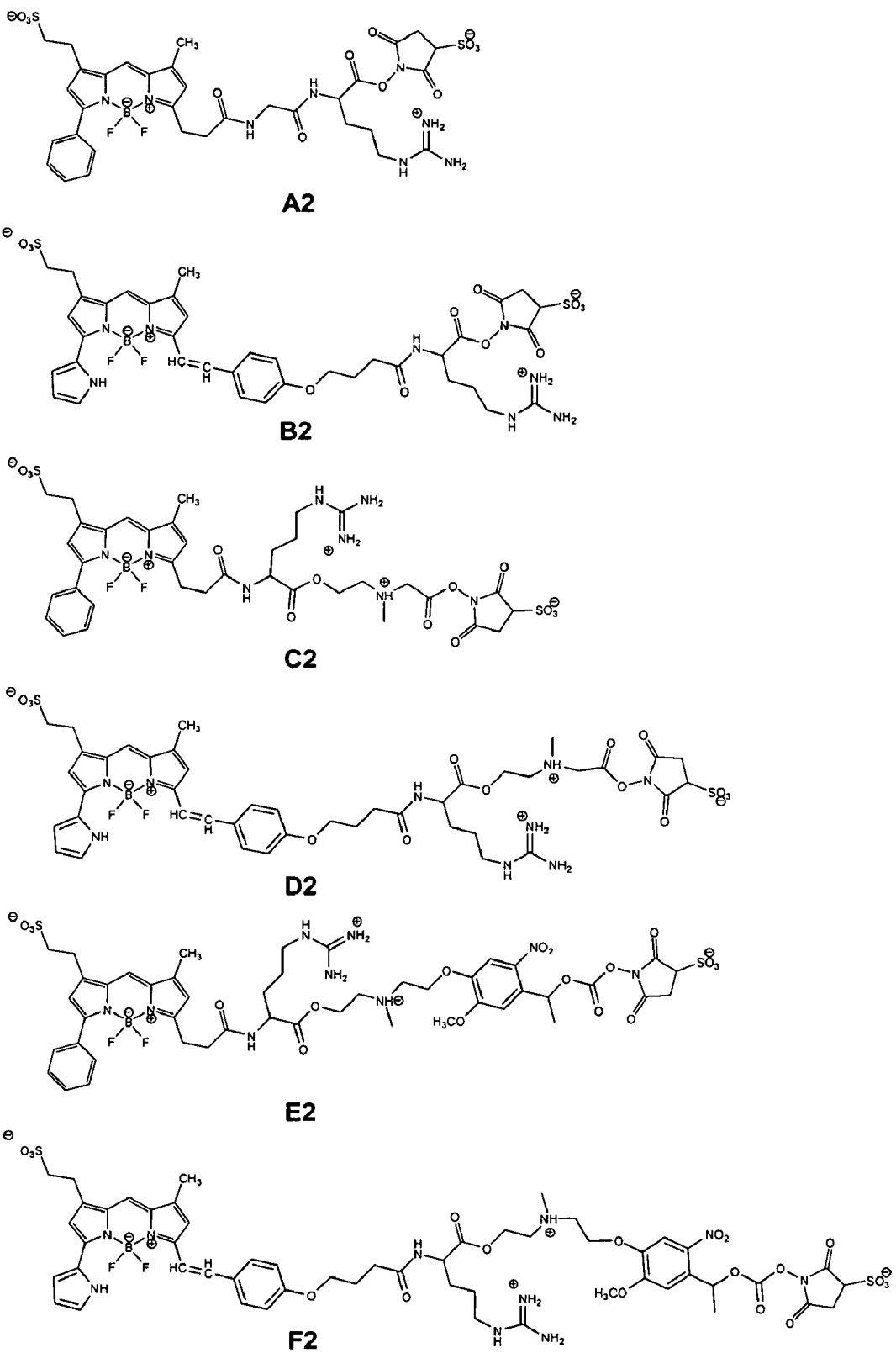
FIGS. 9A and 9B depicts the structures of zwitterionic dyes A2-I2.
Figure 9B:
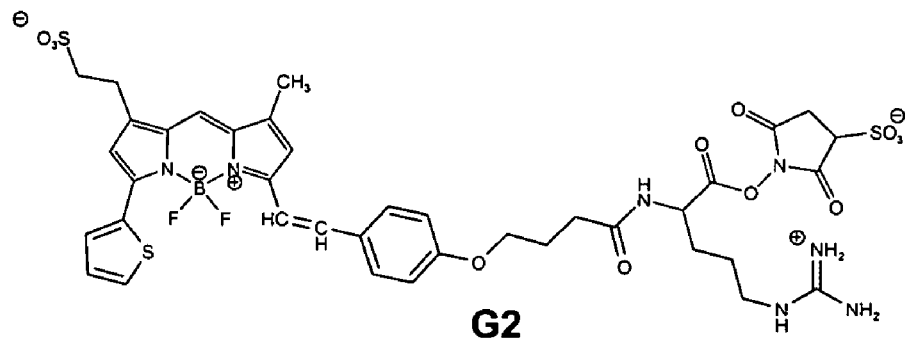
Figure 9B:
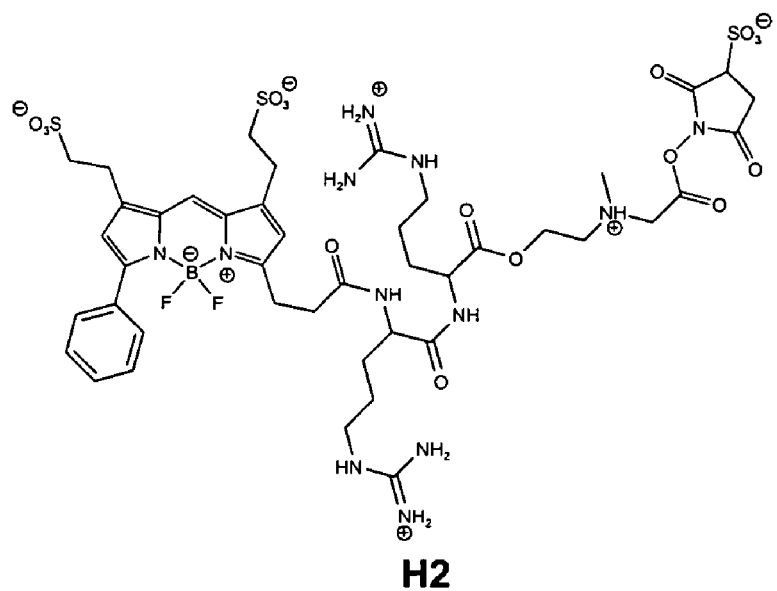
Figure 9B:
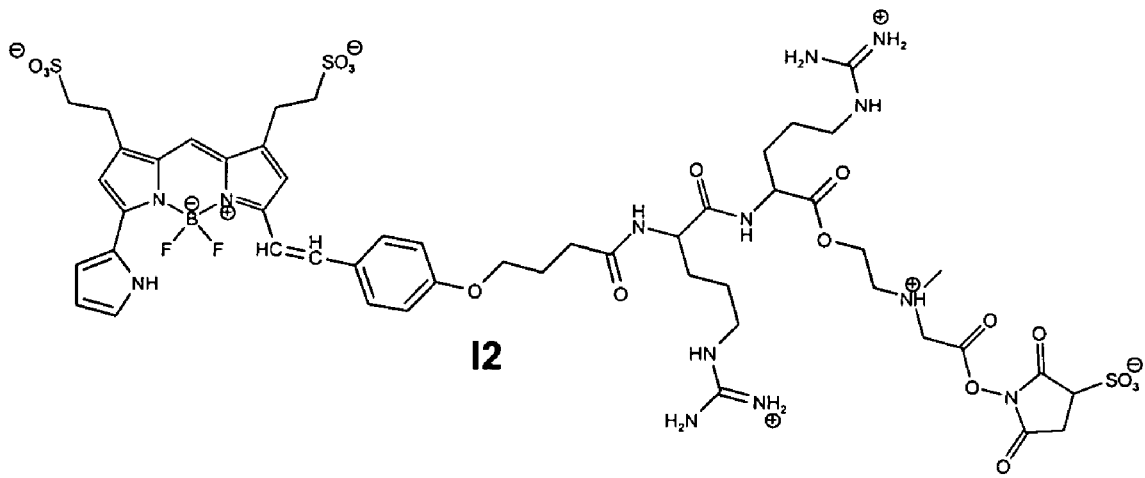

In another embodiment of the invention, the positions of quaternary ammonium and sulfonate groups of the dyes A-I are switched to form dyes A2-I2 as indicated in FIGS. 9A and 9B.

Example 2 describes a route of synthesis for dyes A2-I2.

Figure 10A:
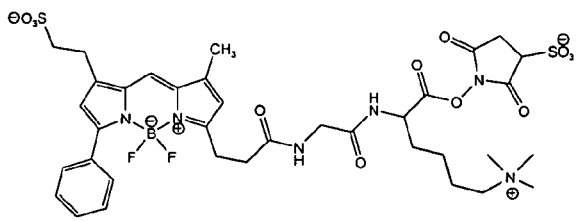
FIGS. 10A and 10B depicts the structures of zwitterionic dyes A3-I3.
Figure 10A:
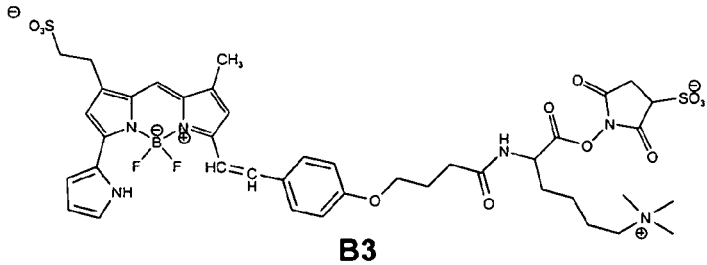
Figure 10A:
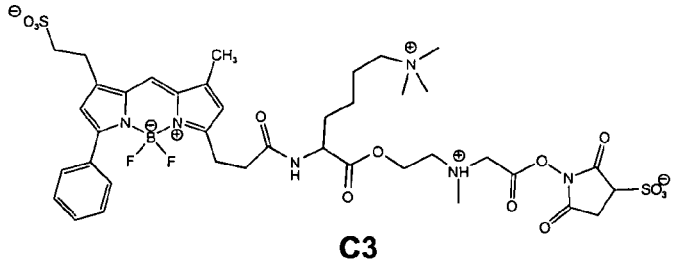
Figure 10A:
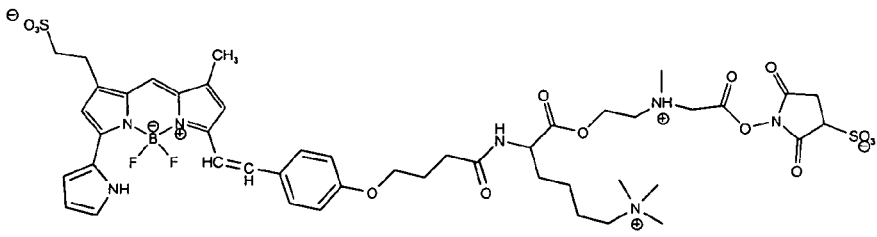
Figure 10A:
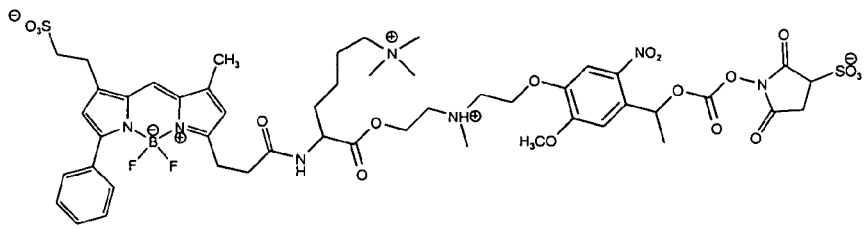
Figure 10A:
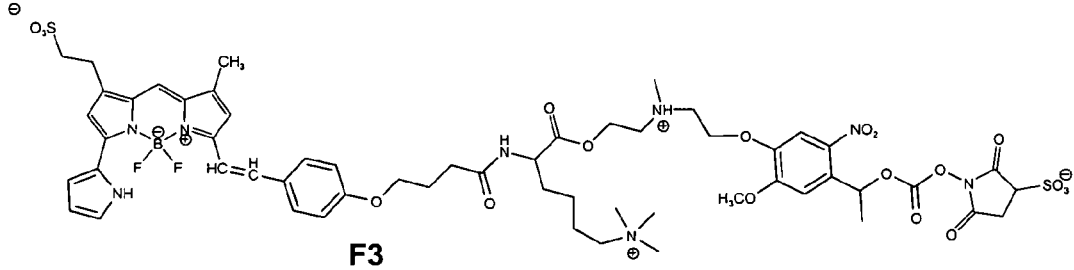
Figure 10B:
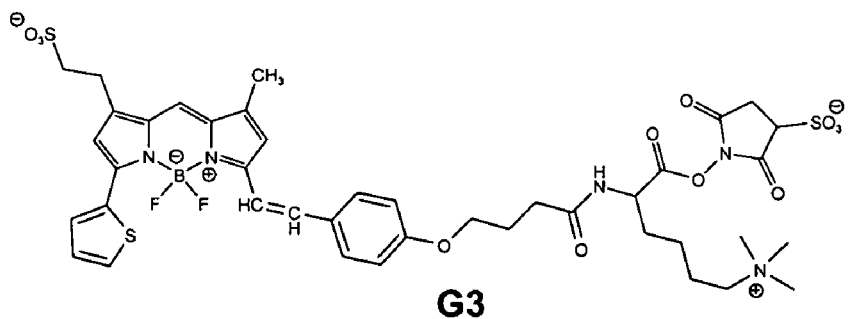
Figure 10B:
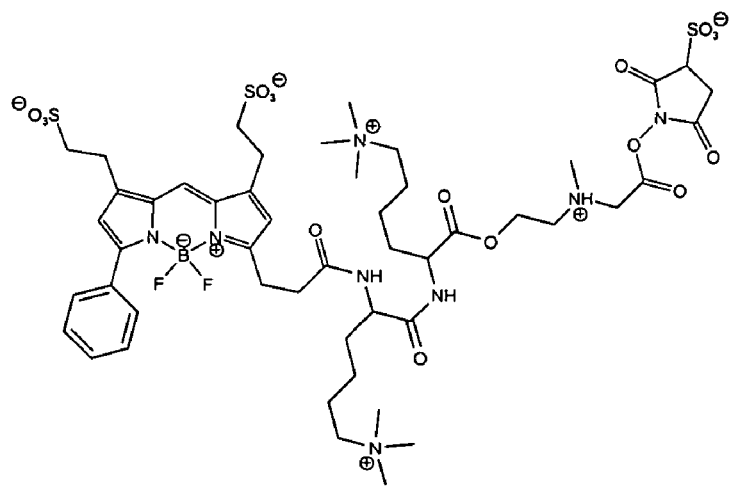
Figure 10B:
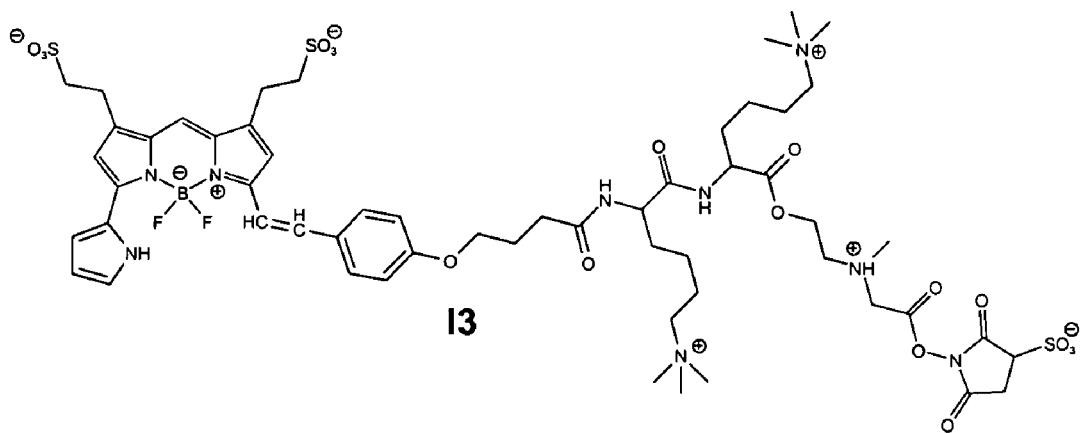

In another embodiment of the invention, the arginine residues of dyes A2-I2 are substituted with trimethylated lysines to form dyes A3-I3 as indicated in FIGS. 10A and 10B.

Example 3 describes a route of synthesis for dyes A3-I3.

There are two general ways to make optical labeling molecules of the invention. The first way is exemplified by Cascade blue or Alexa dyes where the dye structure is relatively polar and compact but there is a net charge on the dye that would substantially alter the isoelectric points of labeled proteins. To overcome this problem, a tail can be designed and added to include nontitratable opposing charges to form nontitratable zwitterionic charge pairs, to add additional zwitterionic charge pairs, to add titratable groups to replace the acid/base properties of protein groups that are modified by the linker, to add an optional cleavable group, to add an optional second label stable isotope group, and to add a linker group, as described above. The second way to make zwitterionic dyes is exemplified by the BODIPY example, where components of the dye are designed, synthesized and assembled to achieve the dye properties desired. Briefly, steps of organic synthesis are designed to incorporate one or more nontitratable zwitterionic charge pairs, to add titratable groups to replace the acid/base properties of protein groups that are modified by the linker, to add an optional cleavable group, to add an optional second label stable isotope group, and to add a linker group, as described above.

In a preferred embodiment, in addition to the zwitterionic dye moiety, the optical labeling molecule further comprises a titratable group moiety and a functional linker. By "titratable group moiety" is meant a group that mimics the acid-base titration of the group labeled on the target molecule. The charge on the group labeled on the target molecule is typically lost when the group labeled on the target molecule forms a covalent bond with the functional linker of the optical labeling molecule. The titratable group moiety replaces the lost charge and thus maintains the isoelectric points of the labeled target molecules. As discussed herein, in a preferred embodiment of the invention, the target molecule is a protein. In this situation, the titratable group replaces the charge lost when the functional linker forms a covalent bound with the protein, thus closely maintaining the protein's isoelectric point. The isoelectric points of proteins are important factors in determining separation of the proteins using techniques based on the charge and size characteristics such as two-dimensional electrophoresis, ion exchange chromatography, or capillary electrophoresis.

In a further preferred embodiment, in addition to the zwitterionic dye moiety and the titratable group moiety, the optical labeling molecule further comprises a functional linker. This linker is used to attach the optical labeling molecule to the target molecule. Linkers are well known in the art; for example, homo- or hetero-bifunctional linkers are well known (see 1994 Pierce Chemical Company catalog, technical section on cross-linkers, pages 155-200, hereby expressly incorporated by reference). Preferred linkers include, but are not limited to, succinimidyl groups, sulfosuccinimidyl groups, imido esters, isothiocyanates, aldehydes, sulfonylchlorides, arylating agents, maleimides, iodoacetamides, alkyl bromides, or benzoxidiazoles.

The linker forms a covalent bond with one or more sites on a target protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration.

In a preferred embodiment, the type and number of proteins to be labeled will be determined by the method or desired result. In some instances, most or all of the proteins of a cell or virus are labeled; in other instances, some subset, for example subcellular fractionation, is first carried out, or macromolecular protein complexes are first isolated, as is known in the art, before dye labeling, protein separation and analysis.

Target proteins of the invention include all cellular proteins. Preferred target proteins include regulatory proteins such as receptors and transcription factors as well as structural proteins.

Further preferred target proteins include enzymes. As will be appreciated by those in the art, any number of different enzymes can be labeled. The enzymes (or other proteins) may be from any organisms, including prokaryotes and eukaryotes, with enzymes from bacteria, fungi, extremeophiles, viruses, animals (particularly mammals and particularly human) and birds all possible. Suitable classes of enzymes include, but are not limited to, hydrolases such as proteases, carbohydrases, lipases; isomerases such as racemases, epimerases, tautomerases, or mutases; transferases, kinases and phosphatases. Preferred enzymes include those that carry out group transfers, such as acyl group transfers, including endo- and exopeptidases (serine, cysteine, metallo and acid proteases); amino group and glutamyl transfers, including glutaminases, γ glutamyl transpeptidases, amidotransferases, etc.; phosphoryl group transfers, including phosphotases, phosphodiesterases, kinases, and phosphorylases; nucleotidyl and pyrophosphotyl transfers, including carboxylate, pyrophosphoryl transfers, etc.; glycosyl group transfers; enzymes that do enzymatic oxidation and reduction, such as dehydrogenases, monooxygenases, oxidases, hydroxylases, reductases, etc.; enzymes that catalyze eliminations, isomerizations and rearrangements, such as elimination/addition of water using aconitase, fumarase, enolase, crotonase, carbon-nitrogen lyases, etc.; and enzymes that make or break carbon-carbon bonds, i.e. carbanion reactions. Suitable enzymes are listed in the Swiss-Prot enzyme database.

Suitable viruses as sources of analytes to be labeled include, but are not limited to, orthomyxoviruses, (e.g. influenza virus), paramyxoviruses (e.g. respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella☐zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like) Suitable bacteria include, but are not limited to, *Bacillus; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C. perfringens*; Cornyebacterium, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *G. lamblia Y. pestis, Pseudomonas*, e.g. *P. aeruginosa, P. putida; Chlamydia*, e.g. *C. trachomatis; Bordetella*, e.g. *B. pertussis; Treponema*, e.g. *T. palladium*; and the like.

In addition, any number of different cell types or cell lines may be evaluated using the labeling molecules of the invention.

Particularly preferred are disease state cell types, including, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cell lines, including, but not limited to, Jurkat T cells, NIH3T3 cells, CHO, Cos, etc. See the ATCC cell line catalog, hereby expressly incorporated by reference.

In one embodiment, the cells may be genetically engineered, that is, contain exogenous nucleic acid, for example, when the effect of additional genes or regulatory sequences on expressed proteins is to be evaluated.

In some embodiments, the target analyte may not be a protein; that is, in some instances, as will be appreciated by those in the art, other cellular components, including carbohydrates, lipids, nucleic acids, etc., can be labeled as well. In general this is done using the same or similar types of chemistry except that the linker moieties may be different and there may or may not be a need for a titratable group in the dye to maintain the pI of the labeled molecule, as will be appreciated by those in the art.

As will be appreciated by those in the art, depending on the target molecule(s), an appropriate linker is chosen.

In a preferred embodiment of the invention, the linker forms a covalent bond with an amine group of the target protein. Examples of linkers that form covalent bonds with amine groups are imidoesters and N-hydroxysuccinimidyl esters, sulfosuccinimidyl esters, isothiocyanates, aldehydes, sulfonylchlorides, or arylating agents. Amine groups are present in several amino acids, including lysine. Lysine ε-amino groups are very common in proteins (typically 6-7/100 of the residues) and the vast majority of the lysines are located on protein surfaces, where typically they are accessible to labeling. In a preferred embodiment of the invention, the more reactive N-terminal amino groups may be pre-labeled near neutral pH with a different amine-reactive group, such as a small acid anhydride with or without an isotopic label to minimize dye-induced shifts in isoelectric focusing after lysine labeling. Small isotope-labeled groups on the N-terminus can be used for independent protein quantitation, using isotope ratio measurements in a mass spectrometer. The surface-exposed lysine amino groups tend to have pKs very close to 10 (Tanford, C. (1962) The interpretation of hydrogen ion titration curves of proteins. *Adv. Protein Chem.* 17: 69-165; Mattew, J. B., et al., (1985) pH-dependent processes in proteins, *CRC Crit. Rev. Biochem* 18: 91-197, each of which are hereby expressly incorporated by reference) react at higher pH and their pKs can be mimicked by (hindered, non-reactive) amino groups added as the titratable group moiety in the optical labeling molecules of the invention.

In another embodiment of the invention, thiol groups of the target protein are used as the linker attachment site. Examples of linkers that form covalent bonds with thiol groups are sulfhydryl-reactive maleimides, iodoacetamides, alkyl bromides, or benzoxidiazoles.

The covalent bond is formed between the functional linker and target protein under conditions well known in the art and further discussed herein.

Figure 11:
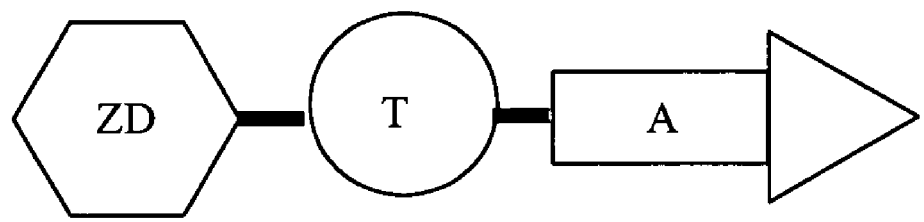
FIG. 11 depicts general structures of an optical labeling molecule comprising a zwitterionic dye moiety (ZD), a titratable group moiety (T) that closely approximates the pK of the group removed from the protein by reaction with the functional linker, and the functional linker (A).
Figure 11:
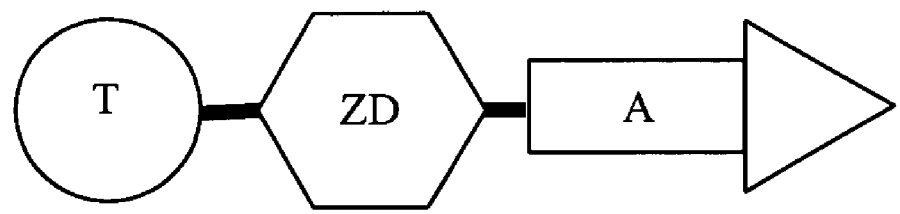

Thus, in a preferred embodiment of the invention, the optical labeling molecule has one or more zwitterionic dye moiety, a titratable group moiety, and a functional linker and has one of the general structures depicted in FIG. 11.

In a preferred embodiment, in addition to the zwitterionic dye moiety, the titratable group moiety, and the functional linker, the optical labeling molecule further comprises a cleavable moiety. By "cleavable moiety" is meant a group that can be chemically, photochemically, or enzymatically cleaved. In a preferred embodiment of the invention, the cleavable moiety is a moiety that forms a stable bond but can be efficiently cleaved under mild, preferably physiological, conditions. In a preferred embodiment, the cleavage site utilizes a photocleavable moiety. That is, upon exposure to suitable wavelengths of light absorbed by the photo-cleavable groups, cleavage of the linker occurs, thereby removing the dye from the protein or other molecule to facilitate further analysis. A particularly preferred class of photocleavable moieties are the O-nitrobenzylic compounds, which can be synthetically incorporated into the zwitterionic labeling dye via an ether, thioether, ester (including phosphate esters), amine or similar linkage to a heteroatom (particularly oxygen, nitrogen or sulfur). Also of use are benzoin-based photocleavable moieties. Nitrophenylcarbamate esters are particularly preferred. A wide variety of suitable photocleavable moieties is outlined in the Molecular Probes Catalog, supra.

By engineering in a cleavable moiety on the optical labeling molecule, the maximum detection sensitivity of the labeling molecule is increased by allowing a high multiplicity of dye labeling that will increase the maximum detection sensitivity, followed by removal of the labeling molecule prior to further analysis. For example, the optical labeling molecule can be removed after protein separation via cleavage of the cleavable moiety prior to mass spectroscopy (MS) analysis. Identification of interesting protein spots on 2D gels for further study is typically accomplished by fluorescent scanning during analysis of the gels, but identification of the proteins contained in those spots is generally accomplished by mass spectrometry. The most generally effective method of identifying proteins and post-translational modifications digests proteins with trypsin or other lysine-specific enzymes, before analysis by mass spectrometry. As is well known in the art, trypsin is an enzyme that specifically cleaves at the basic amino acid groups, arginine and lysine. High multiplicity attachment of optical labeling molecules on amino groups will "cover" some of the most accessible lysine amino groups and if the dyes are not removed they will inhibit trypsin digestion at these sites. In some embodiments, this may be preferred In some embodiments, this may be preferred. Thus, the removal of the dye after protein separation by chemical, photochemical or enzymatic cleavage is preferable in some embodiments.

Figure 12:
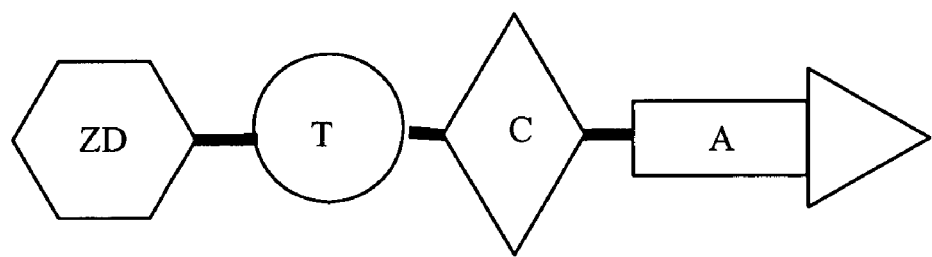
FIG. 12 depicts general structures of an optical labeling molecule comprising a zwitterionic dye moiety (ZD), a titratable group moiety (T) that closely approximates the pK of the group removed from the protein by reaction with the functional linker, a cleavable moiety (C), and the functional linker (A).
Figure 12:
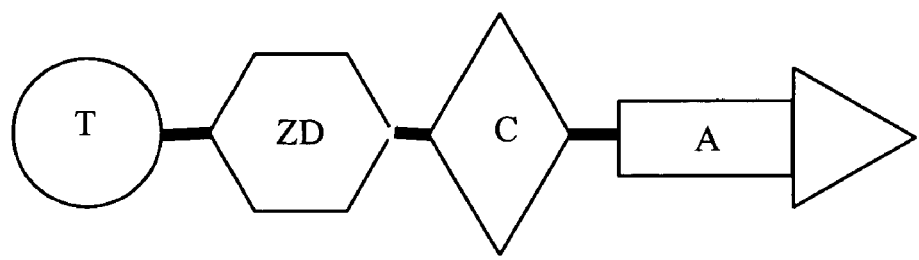
Figure 12:
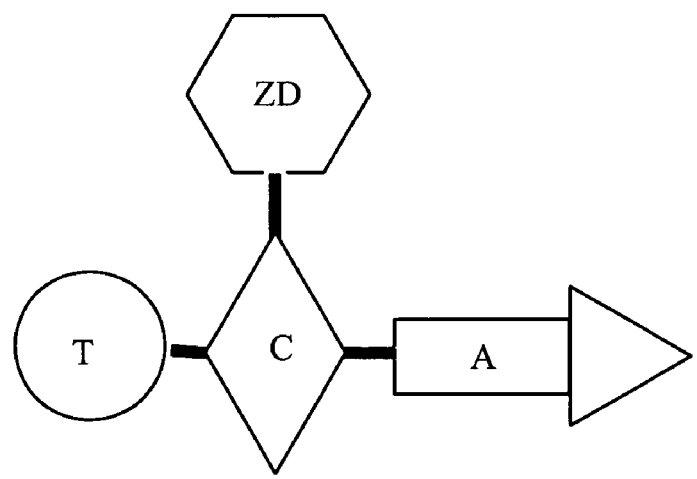

In a further embodiment of the invention, the optical labeling molecule has a zwitterionic dye moiety, a titratable group moiety, a functional linker, and a cleavable moiety and has one of the general structures as depicted in FIG. 12.

In a further embodiment of the invention, the optical labeling molecule comprises a second label in addition to the zwitterionic dye. A second label can, for example, be a stable isotope label, an affinity tag, an enzymatic label, a magnetic label, or a second fluorophore.

In a preferred embodiment of the invention, the optical labeling moiety comprises a zwitterionic dye moiety, a titratable group moiety, a cleavable moiety, a stable isotope moiety, and a functional linker. In a preferred embodiment of the invention, the stable isotope moiety made up of light isotopes. In a further preferred embodiment, the stable isotope moiety is one or more combinations of heavy isotopes. In one embodiment of the invention, the stable isotope is located between the cleavable moiety and the functional linker.

Figure 13:
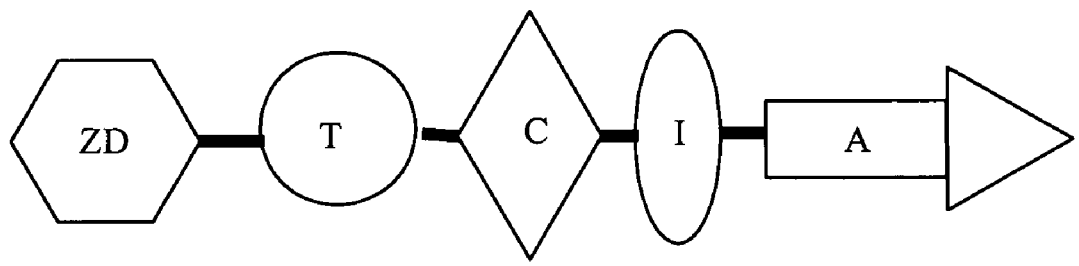
FIG. 13 depicts general structures of an optical labeling molecule comprising a zwitterionic dye moiety (ZD), a titratable group moiety (T) that closely approximates the pK of the group removed from the protein by reaction with the functional linker, a cleavable moiety (C), a second label that is designed to leave a residual isotopic label on the protein when the dye is removed (I), and a functional linker (A).
Figure 13:
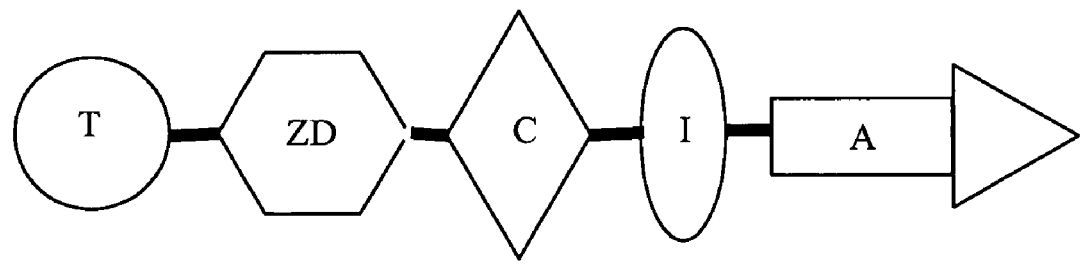
Figure 13:
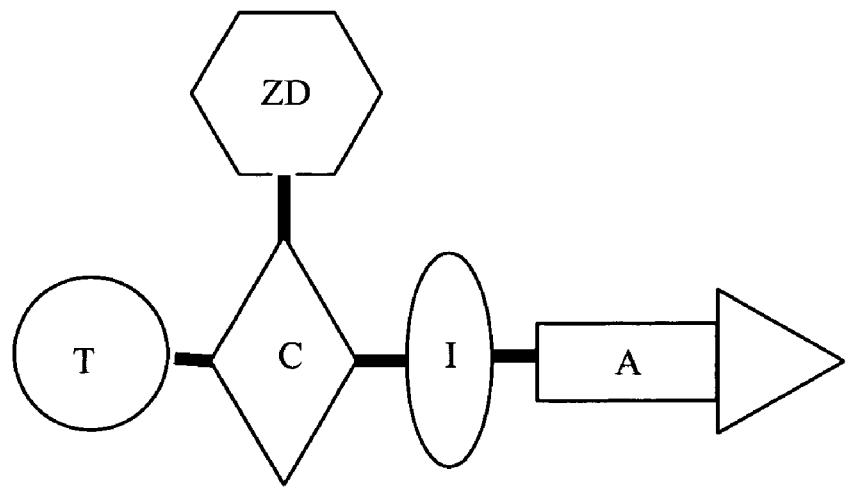

Thus, in a preferred embodiment of the invention, the optical labeling molecule has a zwitterionic dye moiety, a titratable group moiety, a cleavable moiety, a stable isotope moiety, and a functional linker and has one of the general structure as depicted in FIG. 13. With this embodiment, when the cleavable moiety is cleaved, the stable isotope moiety is left on the protein and the relative amount of the protein expressed by the biological system under different stimulus conditions can be quantitated using isotope ratios in a mass spectrometer.

Another embodiment of the invention is a target molecule labeled with an optical labeling molecule as described in any of the previously discussed embodiments.

Once made, the compositions of the invention find use in a wide variety of applications.

One aspect of the invention provides for a method of labeling a protein using any of the above-described optical labeling molecules wherein the optical labeling molecule is contacted with a target protein to form a labeled protein. The event of contacting the target protein with an optical label of the invention is also referred to as a labeling reaction. As is known in the art, conditions that may affect the efficiency of the labeling reaction include the sensitivity of labeling reaction to pH, buffer type, and the salts in the reaction medium. In one embodiment of the invention, the labeling reaction is performed near pH 8.5. Amine-containing buffers are generally avoided to prevent potential cross-reactions with the amine reactive functional linker groups when such groups are used. Preferred buffers include, but are not limited to, phosphate, phosphate/borate, tertiary amine buffers such as BICINE, and borate. Additional agents that may be added to the labeling reaction included various detergents, urea, and thiourea.

The efficiency and progress of the labeling reaction, also referred to as labeling kinetics, and can be measured by quenching the labeling reaction at different times with excess glycine, hydroxylamine or other amine. The number of dyes per labeled protein and the relative fluorescence of the dyes on different labeled proteins can be determined using methods well known to those of skill in the art. For example, the number of optical labeling molecules per labeled protein and the relative fluorescence of the optical labeling molecules on different labeled proteins can be determined by separating the labeled proteins from the free optical label, using HPLC gel filtration with in-line fluorescence and absorbance detection. The ratio of hydrolyzed and unreacted optical label can be determined on the free optical label fraction by RP-HPLC (reverse-phase HPLC), if desired to help optimize labeling conditions. Isolated, labeled proteins can be incubated and run again on gel filtration determine the stability of protein-optical label molecule. (Miyairi S., et al., (1998) Determination of metallothionein by high-performance liquid chromatography with fluorescence detection using an isocratic solvent system. *Anal Biochem.* 258(2):168-75; Mills J S, et al. (1998), Identification of a ligand binding site in the human neutrophil formyl peptide receptor using a site-specific fluorescent photoaffinity label and mass spectrometry, *J Biol. Chem.* 273(17):10428-35; Kwon G, et al., (1993) Synthesis and characterization of fluorescently labeled bovine brain G protein subunits, *Biochemistry*, 32(9):2401-8, each of which is hereby expressly incorporated by reference).

In a further embodiment of the invention, a plurality of target proteins are labeled with different optical labeling molecules of the invention. By "different optical labeling molecule" is meant optical labeling molecules of the invention that are preferably but not necessarily from the same family, but exhibit different optical properties. For example, one family of different optical labeling molecules is a number of optical labeling molecules with fluorescent zwitterionic dye moieties, where each one of the family exhibits a different fluorescence spectra. Preferably, but not required, each optical labeling molecule of the family has similar physical characteristics. By "similar physical characteristics" is meant that each optical labeling molecule of the family has similar size charge and isoelectric point characteristics to minimize any shifts in isoelectric point or ion exchange chromatographic mobility between the labeled and unlabeled proteins. Optical labeling molecules that have similar physical characteristics are preferable to minimize any relative changes in physical characteristics of the protein that arise as a result of the presence of the optical labeling molecule on the protein. For example, the presence of a labeling molecule on the protein may result in a change in the gel mobility or electrophoresis mobility of the labeled protein relative to the unlabeled protein. If each labeling molecule of the family has similar physical characteristics, the plurality of labeled proteins labeled with different dyes will retain sufficiently similar physical characteristics to minimize differences in separation.

One of the most sensitive protein parameters in 2D gel analysis that can be perturbed by dye labeling is the isoelectric point and solubility of the labeled molecule at or near the isoelectric point. 2D gels have modest resolution by mass and so labeling with different numbers of dyes generally does not change the apparent mass in a significant manner on 2D gels. The nontitratable zwitterionic dyes of the invention increase the solubility of proteins especially at the isoelectric point but do not change the isoelectric point of the protein significantly and titratable groups that replace the acid/base behavior of the target of the dye linker group on the protein minimize isoelectric point shifts in the labeled protein. As a result, the plurality of proteins labeled with different dyes generally exhibit virtually the same gel mobility or electrophoresis mobility pattern and will also be very similar to the unlabeled proteins.

In a preferred embodiment of the invention, the family of different optical labeling molecules is selected from dyes A-I (FIGS. 8A and 8B). In another preferred embodiment of the invention, the family of different optical labeling molecules is selected from dyes A2-I2 (FIGS. 9A and 9B). In yet another preferred embodiment of the invention, the family of different optical labeling molecules is selected from dyes A3-I3 (FIGS. 10A and 10B).

The invention finds utility in a number of applications including use in field of proteomics. The optical labeling molecules of the invention can be used to identify "functional proteomes"—namely cellular proteins that change in level of expression and/or post-translational modification in response to physiological stimuli.

It is an aspect of the invention to provide optical labeling molecules with improved properties for use in multiplex detection reactions of proteins in proteomics. Thus, the invention provides for a family of different optical labeling molecules for use in labeling a plurality of target proteins. As discussed above, each member of the zwitterionic dye labeling reagent family exhibits different optical properties, however, each optical labeling molecule of a dye family has quite similar physical characteristics to other optical labeling molecules of the same family.

In general, a proteomics experiment typically involves the analysis of the proteins present in a cellular extract of the intact organism, tissue, cell or subcellular fraction before and after exposure to a particular physiological stimulus. In one embodiment, proteins that are present in the extract of the cells prior to exposure to the physiological stimuli are labeled with one of the optical labeling molecules. Proteins that are present in the extract of the cells after exposure to the physiological stimuli are labeled with a different one of the optical labeling molecule family, after different strengths of physiological stimuli are applied. Additional samples may be labeled with additional different optical labeling molecules. The dye labeled proteins from two or more cellular extracts are mixed and then simultaneously separated and analyzed by observing the optical signals of the separated proteins, thus permitting the identification of the proteins which are detectably altered in expression level or post-translational modification state in response to the stimuli of interest and facilitating a further focused study of these proteins and their post-translational modifications. In one embodiment of the invention, the presence or absence of the labeled proteins is analyzed to determine if a specific protein is affected by the presence or absence of the physiological stimuli. In a further embodiment of the invention, the relative quantity (or ratios of expression) of the specific labeled proteins is determined.

In a preferred embodiment, the plurality of different labeled proteins are separated prior to determining the ratios of expression or post-translational modification of the different labeled proteins. The different labeled proteins may be separated using, for example, 1D gel electrophoresis, 2D gel electrophoresis, capillary electrophoresis, 1D chromatography, 2D chromatography, 3D chromatography, or mass spectroscopy. In a preferred embodiment of the invention, the large number of labeled proteins are separated by 2D gel electrophoresis and the relative amounts of the proteins in different spots are determined by laser densitometry and multiplex analysis of the strength of the fluorescence of the different dye signals.

The effect of dye labeling on protein solubility and mobility during separation techniques, including two-dimensional electrophoresis analysis, can also be assessed using methods known in the art. For example, the solubility of labeled proteins can be measured by first radioactive N-acetyl labeling, largely of N-terminal groups near neutrality, followed by fluorescent dye labeling of the epsilon amino groups of lysine at elevated pH. An alternative method of radioactive labeling will reduce sulfhydryl groups with tributyl phosphine (TBP) and/or tricarboxyethyl phosphine (TCEP) or tri-(2 cyano ethyl)phosphine and label the sulfhydryl groups with radioactive iodoacetaarude, followed by amino group dye labeling. Next, 2D gels can be run on the radioactively tagged and labeled proteins after low (substoichiometric), medium (one or two optical labeling molecules per protein) and high labeling (many optical labeling molecules per protein). The gels can then be scanned for fluorescence and the location of radioactive spots can be measured by phosphorimaging on the same instrument, for example the BioRadFX Fluorescent Gel Scanner and Phosphoimager. The solubilities of labeled proteins can be assessed from changes of retention of proteins on the IEF strips and band streaking in the second dimension, which occurs with insufficient solubility.

Any labeling molecule-induced shifts in protein patterns can be monitored and the expected reduction of shifts assessed using the dyes with titratable groups. The labeling conditions can be optimized for maximum sensitivity with minimum acceptable mobility shifts.

In yet a further aspect of the invention, the different labeled proteins are further analyzed to determine the relative quantity of each different labeled protein. The relative quantity of the different labeled proteins can be determined, for example, by measuring the relative intensity of the optical signal emitted by each of the different labeled proteins.

In a further aspect of the invention, the different labeled proteins are further analyzed to determine absolute quantity. Absolute quantity of a labeled protein can be determined, for example, by including a known amount of an optically labeled protein as an internal standard. Absolute quantity can also be determined by including a known amount of an isotopically-labeled protein or peptide as an internal standard.

In yet a further aspect of the invention, a cleavable group moiety is present on the optical labeling molecule between the zwitterionic dye moiety and the functional linker moiety. After separating the different labeled proteins as discussed above, the cleavable moiety is cleaved to remove the optical labeling molecule from the target protein. The target protein can then be analyzed, for example, using mass spectral techniques (Tao, W. A. and Aebersold, R., (2003) Advances in quantitative proteomics via stable isotope tagging and mass spectrometry, *Current Opinion in Biotechnology*, 14:110-188; Yates, J. R. III (2000) Mass spectrometry. From genomics to proteomics, *Trends Genet*. 16: 5-8, each of which is hereby expressly incorporated by reference).

In a further aspect of the invention, the various post-translational modifications are identified. Post-translational modifications include phosphorylation, methionine oxidation, cysteine oxidation to sulfenic acid, tyrosine nitration, thiol nitrosylation, disulfide formation, glycoslyation, carboxylation, acylation, methylation, sulfation, and prenylation.

In a preferred embodiment of the invention, the phosphorylation state of the proteins in the cells is determined. In this embodiment, unstimulated cells are labeled with $^{33}$P phosphate and the protein extract of the cells labeled with a first optical labeling molecule. Cells that have been exposed to a growth factor or other stimulus are labeled with $^{32}$P phosphate and a second different optical labeling molecule. Preferably, the first and the second optical labeling molecules are chosen from the same set of optical labeling molecules so that the optical signal is different but the physical characteristics are similar. The labeled extracts of the cells are mixed and simultaneously separated by a method described above. The labeled extracts are analyzed with optical scanning to determine protein expression ratios between the stimulated and unstimulated cells. The gel is sandwiched between two phosphoimaging detector plates with a thin metal foil in between the gel and the phosphoimager plate on one side of the gel. The phosphoimager plate on the side with no foil responds to $^{32}$P+$^{33}$P whereas the phosphoimager plate on the side with the metal foil only detects the $^{32}$P since the beta radiation from the $^{33}$P is blocked by the thin metal foil. The phosphoimager plates are read and the ratios of the signals for the two plates are analyzed to determine the relative amount of phosphorylation on each protein on the gel. The methods can be used to determine the levels of phosphorylation of each protein on a gel by using antibodies or other labels, e.g. antiphosphothreonine antibodies (that are well known) and a chemical labeling method for phosphoserine and phosphothreonine groups on gel-separated proteins. After the proteins are separated on the gel and expression ratios measured by laser scanning the gels, the proteins can either be further analyzed on the gel or transferred to blotting membranes for further analysis.

Figure 7A:
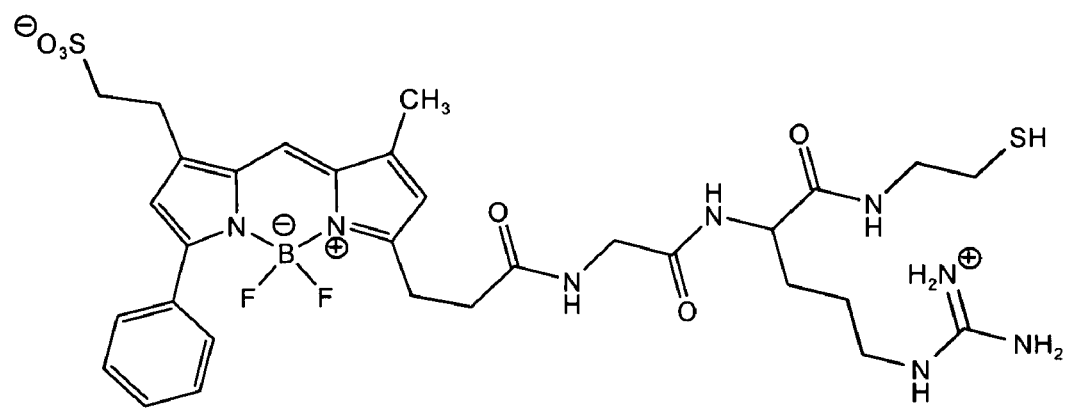
FIGS. 7A and 7B depict two examples of a zwitterionic optical labeling molecule that can be used to label phosphorylation sites on proteins after beta-elimination of phosphates from serine and/or threonine side chains.
Figure 7B:
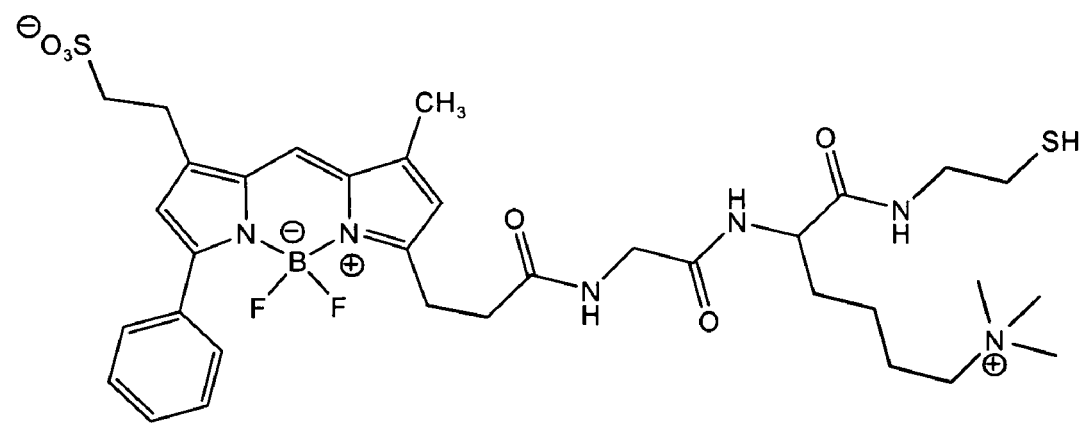

In order to measure the phosphoserine and phosphothreonine levels on each protein, one embodiment is to incubate the gel or blot in strong base (e.g. 1 M barium hydroxide) at 60 degrees C. for several hours to beta-eliminate the phosphate groups from phosphoserine and phosphothreonine. A dye similar to or identical to one of the dyes shown in FIG. 7A or FIG. 7B is reacted with the modified proteins, the excess unreacted dye is rinsed away and fluorescence signals that reflect protein phosphorylation are measured. Other methods are available to detect other post-translational modifications of proteins by pre- or post-labeling on gels where protein expression ratios have been measured. Thus, the protein multiplex methods of the invention can be extended for with simultaneous monitoring of changes in phosphorylation, as well as the changes in the level of the protein and other postranslational modifications of the proteins.

A further aspect of the invention provides for methods of determining whether a particular protein is exposed to the surface of its native environment. In one embodiment of the invention, a first optical labeling molecule is used to label exposed target proteins on the surfaces of cells, isolated organelles or isolated multiprotein complexes. The cell or organelle membranes or the multiprotein complex structure are then disrupted with detergents and/or chaotropic compounds and the interior groups labeled with a second, different optical labeling molecule. The sample is then separated by a method described above. Those proteins labeled with the first optical labeling molecule are proteins exposed to the surface of the cell, organelle or multiprotein complex. Those proteins labeled with the second optical labeling molecule are proteins that are not exposed to the surface of cell, organelle or multiprotein complex. In a preferred embodiment of the invention, the labeled proteins are isolated and identified, as described above.

In addition, as will be appreciated by those in the art, the compositions of the invention can be used as optical labels in any standard application of optical labels. For example, the analysis of single proteins can be done. A wide variety of techniques and applications are described in the gth ed. of the Molecular Probes Catalog and references cited therein. Similarly, certain nucleic acid analyses such as gene expression and genotyping utilize dyes, which can be the dyes of the invention. For example, capillary electrophoresis separations of both proteins and nucleic acids can rely on pI, and the dyes of the invention can be used in these applications.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are hereby expressly incorporated by reference.

Additional references, each of which is hereby incorporated by reference:

1. Holt, L. J., et al., (2000) The use of recombinant antibodies in proteomics. *Curr. Opin. Biotechnol.* 11: 445-449.
2. Unlu, M., et al., (1997) Difference gel electrophoresis: a single gel method for detecting changes in protein extracts, *Electrophoresis* 18: 2071-2077.
3. Griffiths, W. J. (2000) Nanospray mass spectrometry in protein and peptide chemistry. *EXS* 88: 69-79.
4. Borchers, C., et al., (2000) Identification of in-gel digested proteins by complementary peptide mass fingerprinting and tandem mass spectrometry data obtained on an electrospray ionization quadrupole time-of-flight mass spectrometer, *Anal. Chem.* 72: 1163-1168.
5. Belov, M. E., et al., (2000) Zeptomole-sensitivity electrospray ionization—Fourier transform ion cyclotron resonance mass spectrometry of proteins, *Anal. Chem.* 72: 2271-2279.
6. Gatlin, C. L., et al., (1998) Protein identification at the low femtomole level from silver-stained gels using a new fritless electrospray interface for liquid chromatography-microspray and nanospray mass spectrometry, *Anal. Biochem.* 263: 93-101.
7. Ogueta, S., et al., (2000) Identification of phosphorylation sites in proteins by nanospray quadrupole ion trap mass spectrometry, *J. Mass Spectrom.* 35: 556-565.
8. Loo, J. A., et al., (1999) High sensitivity mass spectrometric methods for obtaining intact molecular weights from gel-separated proteins, *Electrophoresis* 20: 743-748.
9. Cordwell, S. J., et al., (2000) Subproteomics based upon protein cellular location and relative solubilities in conjunction with composite two-dimensional electrophoresis gels. *Electrophoresis* 21: 1094-1103.

EXAMPLE 1

Synthesis of Dyes A-I

The synthetic scheme and description below provides an example of synthesis for dyes A-I (FIGS. 8A and 8B). All references listed below are hereby expressly incorporated by reference.

The synthesis of engineered dye A for proteomic analyses requires sequential coupling of the synthetic boradiazaindacene-3-propionic acid, succinimidyl ester 1, prepared as outlined in Scheme 1, with glycine and L-Cys(SO$_3$H)—OH which will provide acid 2. Direct coupling of I with Gly-L-Cys(SO$_3$H)—OH leads directly to 2. Activation (Delfino, J. M., et al., (1993) Design, Synthesis, and Properties of a Photoactivatable Membrane-Spanning Phospholipidic Probe. *J. Am. Chem. Soc.*, 115: 3458-3474) of 2 in acetonitrile with commercially available N-hydroxysulfosuccinimide sodium salt (3) and DMAP followed by addition of DCC will generate A. The synthesis of 1 commences with the known pyrrole 4 (Bray, B. L.; et al., (1990) *J. Org. Chem.*, 55, 6317) and the readily available pyrrole 11 (Muchowski, J. M. and Hess, P., "Lithiation of the dimer of 3-bromo-6-dimethylamino-1-azafulvene. Efficacious synthesis of 4-mono- and 4,5-disubstituted pyrrole-2-carboxaldehydes." (1988) *Tetrahedron Lett.*, 29(26), 3215). Bromination of 4 using NBS provided 5 which underwent Suzuki coupling with phenylboronic acid to yield 2-phenyl-4-formylpyrrole 6. Ester 7 was obtained through a Doebner condensation of 6 with mono-ethyl malonic acid followed by catalytic hydrogenation of the resulting olefin. Conversion of the ester functionality in 7 to the corresponding dimethylamine was carried out in two steps. Treatment of 7 with dimethylamonium chloride in the presence of trimethyl aluminum led to the corresponding N,N-dimethyl amide which was subsequently reduced into the amine by treatment with lithium aluminum hydride (LAH), formylated under the Vilsmeier-Haack reaction conditions, and treated with methyliodide to give way to formyl pyrrole 8 which upon condensation with pyrrole 11 afforded 9. Exposure of 9 to borontrifluoride etherate in the presence of Hunig's base using a modification of Lugtenburg's protocol (Vos de Wael, E., et al., (1977) Pyromethene-BF$_2$ complexes (4,4"-difluoro-4-bora-3a,4a-diaza-s-indacenes), Synthesis and luminescence properties. *Recl. Trav. Chim. Pays-Bas* 96, 306-309) gave rise to the difluoroboradiaza-indacene 10. Preparation of the succinimidyl ester 1 required treatment of 10 with N-hydroxysuccinimide and DCC in acetonitrile. Manipulation of the resulting carbonyl groups is straightforward.

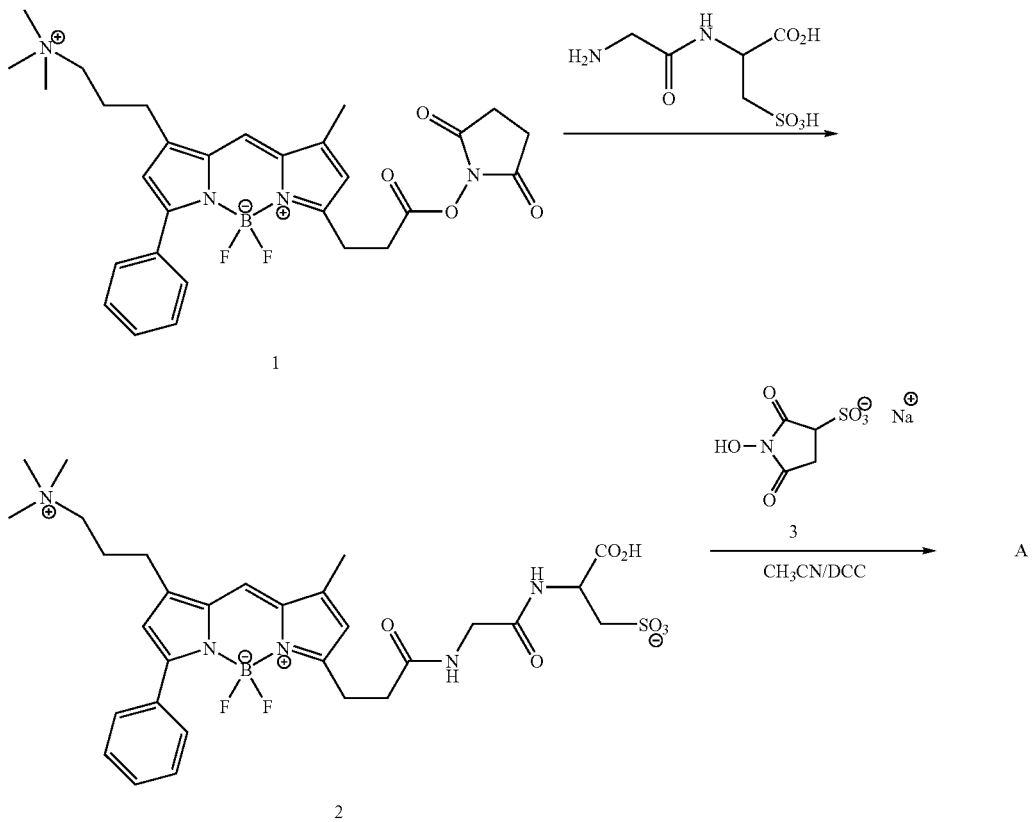

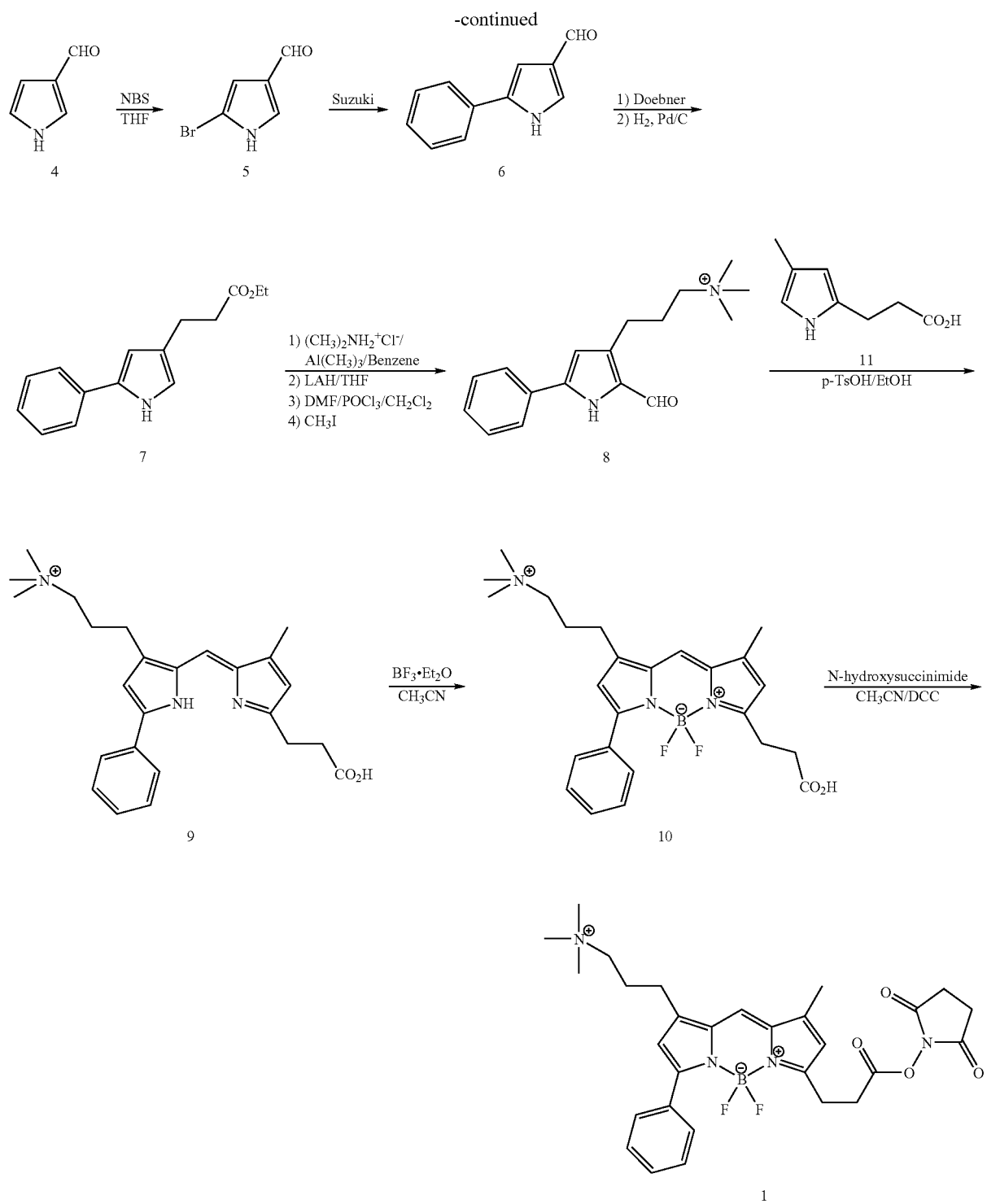

The synthesis of dye B requires condensation of the synthetic boradiazaindacene aldehyde 14 with the readily available ylid 13 leading to 15. Formation of the corresponding sulfosuccinimidyl ester, followed by addition of L-Cys(SO$_3^-$ Na$^+$)—OH, provides 16 which can be transformed into the target dye B employing 3. The required aldehyde 14 is prepared from the readily available pyrrole 17a (Sambrotta, L., et al., (1989) Synthesis of 8-Demethyl-8-Formyl Protoporphyrin IX and of 8-Demethyl Protoporphyrin IX, *Tetrahedron* 45: 6645-6652.) and the known pyrrole 21 (Barton, D. H. R, et al., (1990) A Useful Synthesis of Pyrroles from Nitroolefins, *Tetrahedron* 46[21], 7587-7598, hereby expressly) as illustrated in Scheme 2.

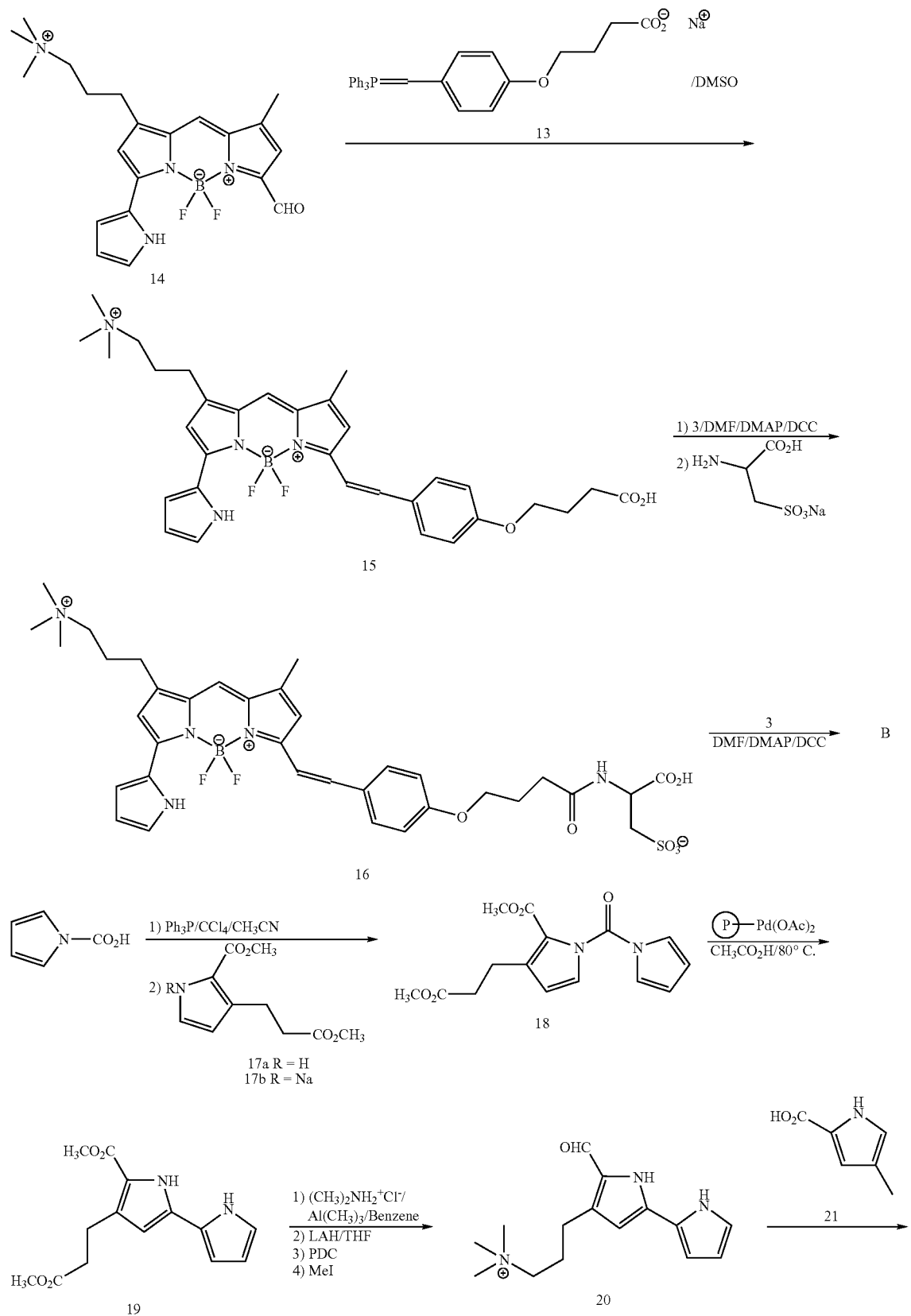

-continued

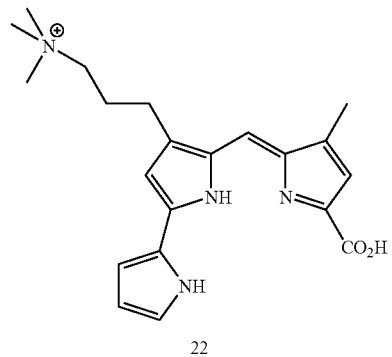

22

Employing the two-step protocol of Boger (Boger, D. L., and Patel, M. (1988) Total Synthesis of Prodigiosin, Prodigiosene, and Desmethoxyprodigiosin: Diels-Alder Reactions of Heterocyclic Azadienes and Development of an Effective Palladium (II)-Promoted 2,2'-Bipyrrole Coupling Procedure, *J. Org. Chem.*, 53, 1405-1415) for the preparation of 2,2'-bispyrroles, pyrrole-1-carboxylic acid is treated with triphenylphosphine-carbon tetrachloride followed by the addition of the sodium salt (17b) of pyrrole 17a, thus giving rise to the 2,2'-bispyrrole 18. Intramolecular palladium (II)-promoted 2,2'-bispyrrole coupling of 18 using stoichiometric, polymer-supported palladium (II) acetate (2-3% Pd, 1% cross-linked polystyrene) affords 19, a key precursor on the synthetic pathway to 14. Selective transformation of the propionate side chain into a trimethylamino propyl side chain followed by conversion of the remaining carbomethoxy group into the required aldehyde 20, sets the stage for condensation with pyrrole 21 leading to direct formation of 22. Transformation of 22 into its pyrromethane-BF$_2$ complex, as described above, and subsequent conversion of the acid functionality into the required aldehyde generates 14. There is ample precedent in the work of Lugtenburg (Vos de Wael, E., et al., (1977), *Recl. Trav. Chim. Pays-Bas* 96, 306-309), suggesting that only the desired pyrromethane-BF$_2$ complex will form.

The preparation of engineered dye C shown in Scheme 3, necessitates coupling of carboxylic acid succinimidyl ester 1 with commercially available L-Cys(SO$_3$+Na$^-$)—OH leading to acid 23. Esterification with the known protected ethanolamine 24 (Powell, J., et al., (1986) Lithium Aluminum Hydride Reductions; A New Hydrolysis Method for Intractable Products, *Synthesis Communications* 338-340) provides, after cleavage of the TBS group and oxidation of the resultant alcohol 25, carboxylic acid 26. The conversion of 26 into sulfosuccinimidyl ester dye C is carried out as detailed above.

Scheme 3

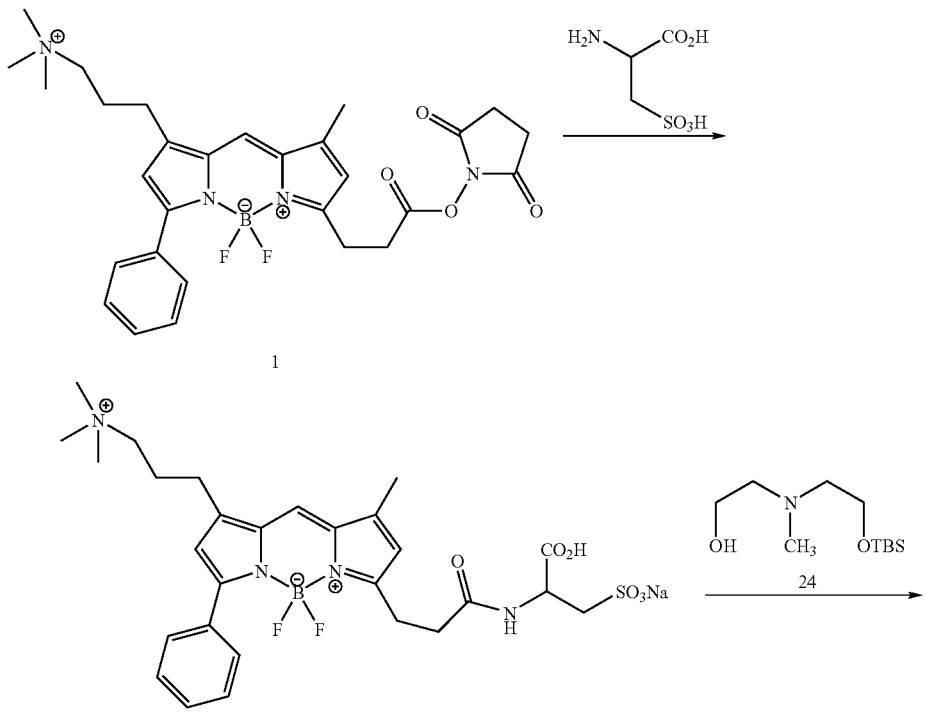

-continued

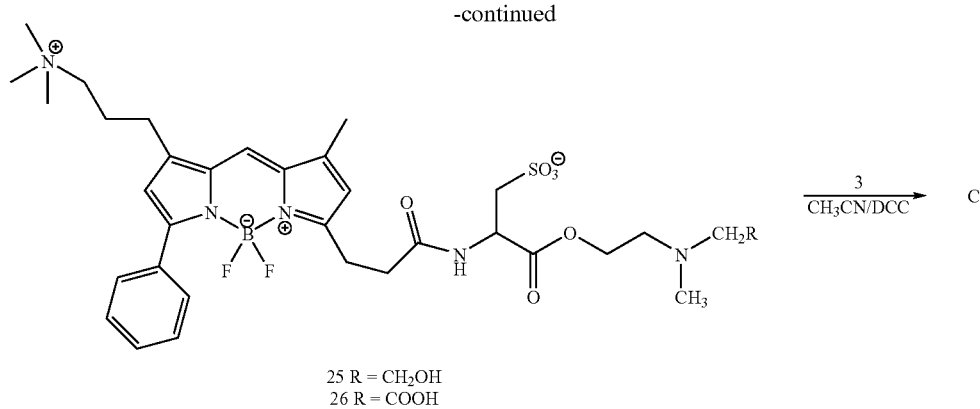

25 R = CH₂OH
26 R = COOH

The elaboration of D is realized by conversion of carboxylic acid 15 into its corresponding sulfosuccinimidyl ester. Following the protocol detailed above for the conversion of 1 into C leads to D.

The synthesis of E (Scheme 4) requires coupling of the carboxylic acid sulfosuccinimidyl ester 27, derived from 23, with 24 followed by the cleavage (TBAF, HOAc, THF) of the silyl protecting group and subsequent conversion (TsCl, pyr, NaI, acetone) of the alcohol into iodide 28. Alkylation of the phenoxide anion derived from 32 with iodide 28 gives rise to 33. Completion of the synthesis of E requires 1) reduction (NaBH₄) of the methyl ketone functionality, 2) coupling of the resultant alcohol 34 with the new reagent 38 leading to 39 and 3) brief exposure of 39 to trimethyl silyl iodide, which leads, upon aqueous workup, to E. The required aromatic piece 32 is prepared from commercially available acetovanillone 29, as outlined in Scheme 5, using the protocol of Åkerblom (Akerblom, E. B., et al., (1998) Six new photolabile linkers for solid-phase synthesis. 1. Methods of preparation. *Mol. Divers.*, 3, 137-148). The novel reagent 38 is prepared from the commercially available sulfo-NHS acetate 35 as detailed in Scheme 6. The methylation of sulfonate anions is well documented in the literature (Trujillo, J. L. and Gopalan, A. S. (2000) Facile Esterfication of Sulfonic Acids and Carboxylic Acids with Triethylorthoacetate, *Tetrahedron Letters* 34, 7355-7358), as well as the treatment of N-hydroxysuccinimide with bis(trichloromethyl) carbonate (Konakahara, T., et al., (1993) A Convenient Method for the Synthesis of Activated N-Methylcarbamates, *Synthesis* 103-106).

Scheme 4

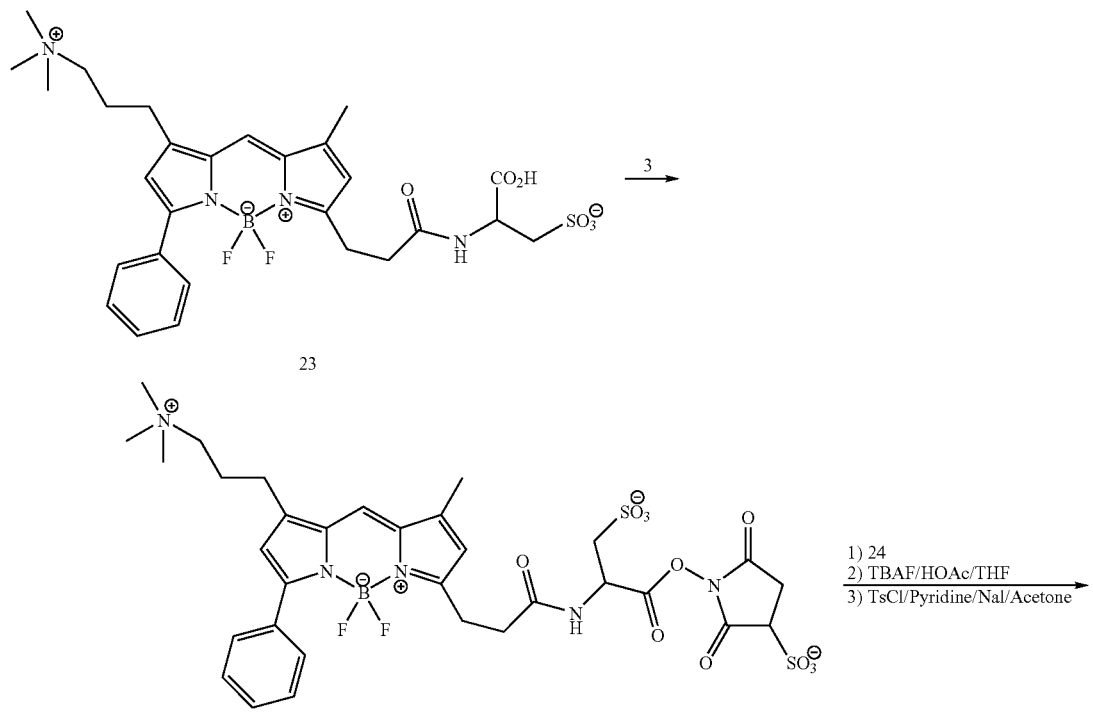

-continued
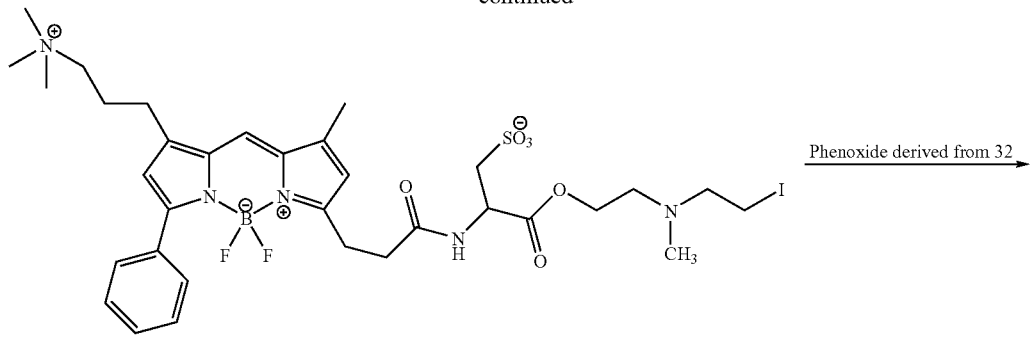
28
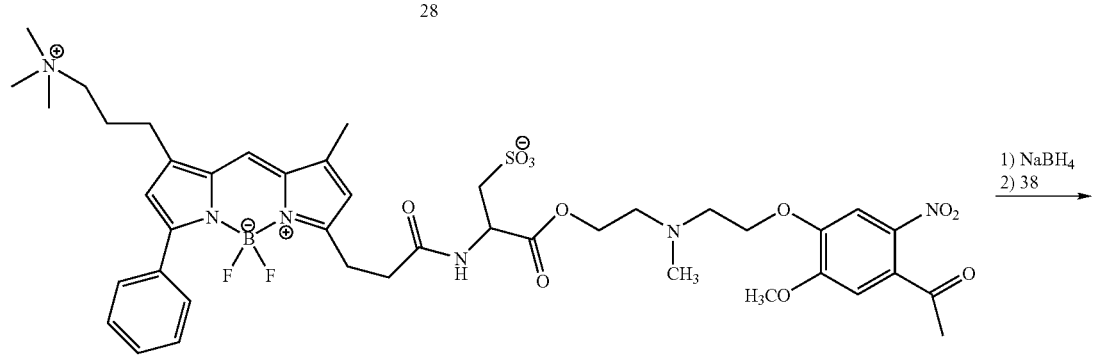
33
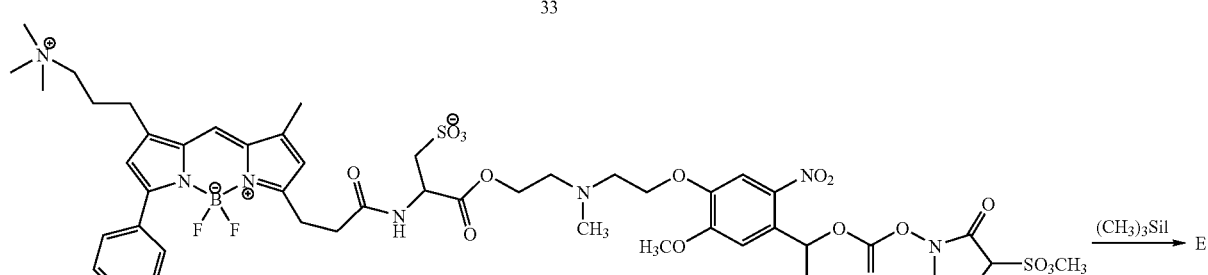
39
Scheme 5
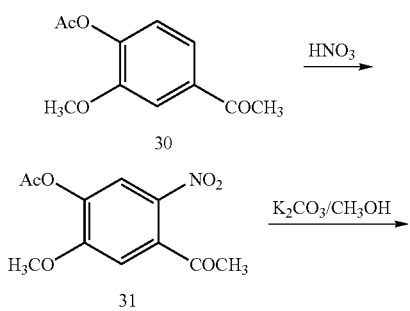
-continued
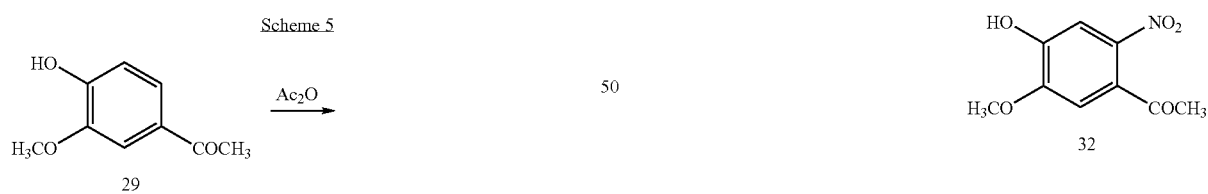

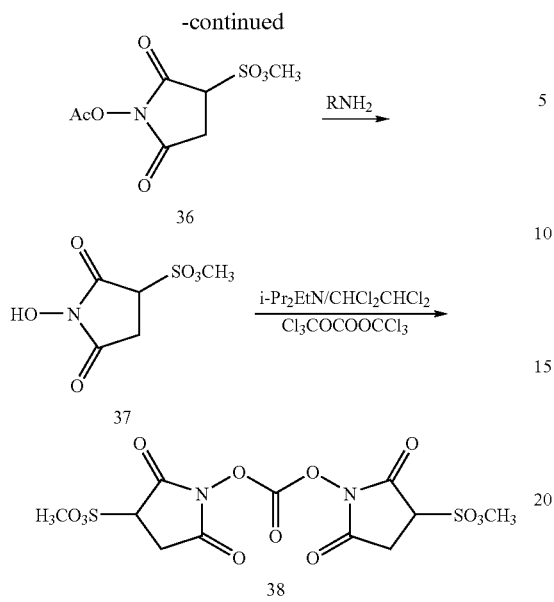

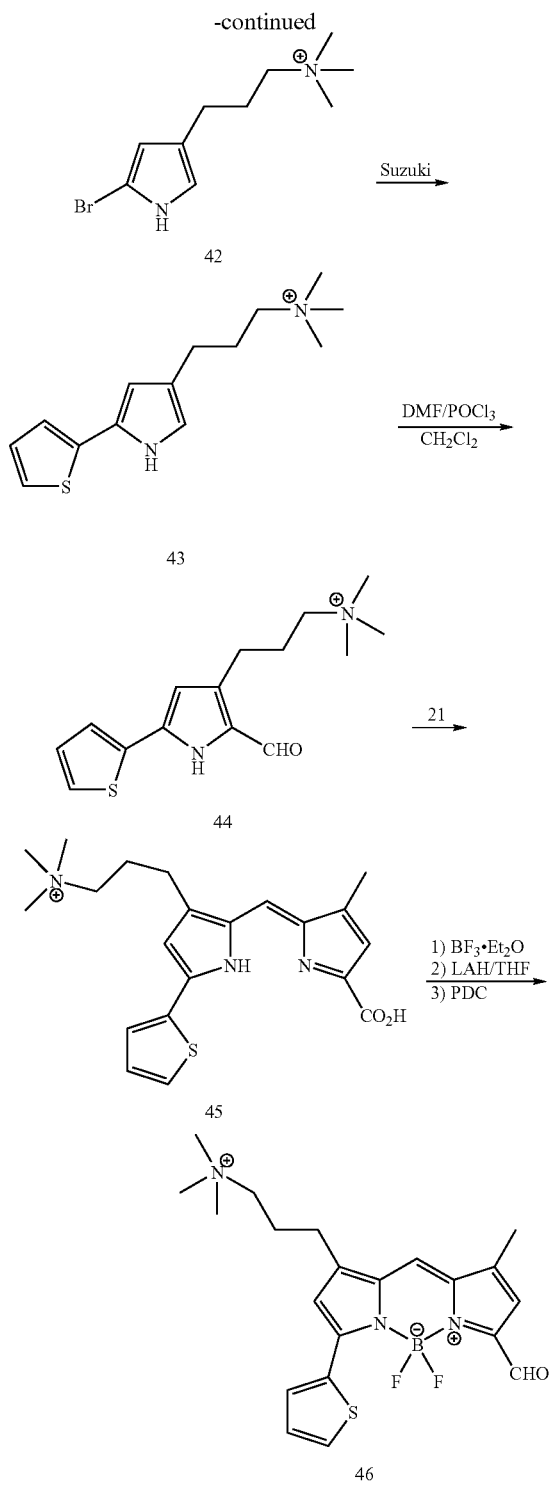

The construction of F commences with carboxylic acid 16 and employs the same protocol that is detailed above for the synthesis of E.

The synthesis of the thienyl boradiazaindacene G (Scheme 7) requires synthesis of the pyrrole 42 from the bromopyrrole 5 via chemistry described for the synthesis of 8. Coupling of 42 with 2-bromothiophene leads to the thienyl pyrrole 43, which upon formylation produces 44. Coupling of 44 with pyrrole 21 affords 45, which upon conversion of the acid functionality into the required aldehyde and subsequent exposure to borontrifluoride etherate gives rise to 46. The transformation of 46 into G utlizes the protocol outlined above for the conversion of 14 into dye B.

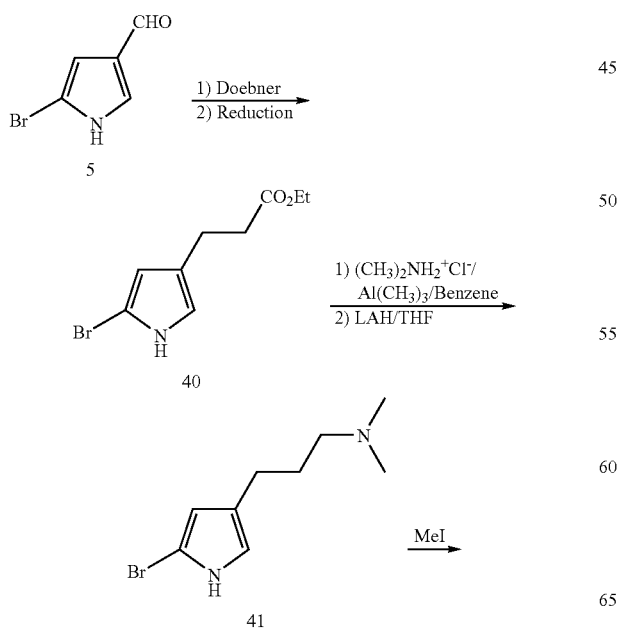

The preparation of H (Scheme 8) requires coupling of the formyl pyrrole 8, prepared as detailed above, with pyrrole 47, whose synthesis is described below. The coupled material 48 is converted as detailed above into the difluoroboradiazaindacene 49. The transformation of 49 into H follows the protocol discussed above for the preparation of C with the minor modification that a quaternized lysine residue is incorporated into the peptide chain. Pyrrole 47 is synthesized from the known pyrrole 50 (Muchowski, J. M. and Hess, P., (1988)

*Tetrahedron Lett.*, 29(26), 3215) as illustrated in Scheme 8. Selective reduction of the more reactive ester followed by protection of the resultant hydroxyl as a silyl ether followed by straightforward transformation of the remaining ester into a formyl group provides 51. Chain extension via an Emmons reaction followed by reduction of the olefin generates 52. Protection of the pyrrole nitrogen followed by sequential cleavage (TBAF) of the silyl ether, a Finkelstein reaction (MsCl; NaI acetone) and displacement with potassium thioacetate affords 53. Exposure of 53 to $K_2CO_3$/MeOH gives way to the corresponding thiol which upon oxidation, methylation, cleavage of the BOC group and hydrolysis of the esters provides 47.

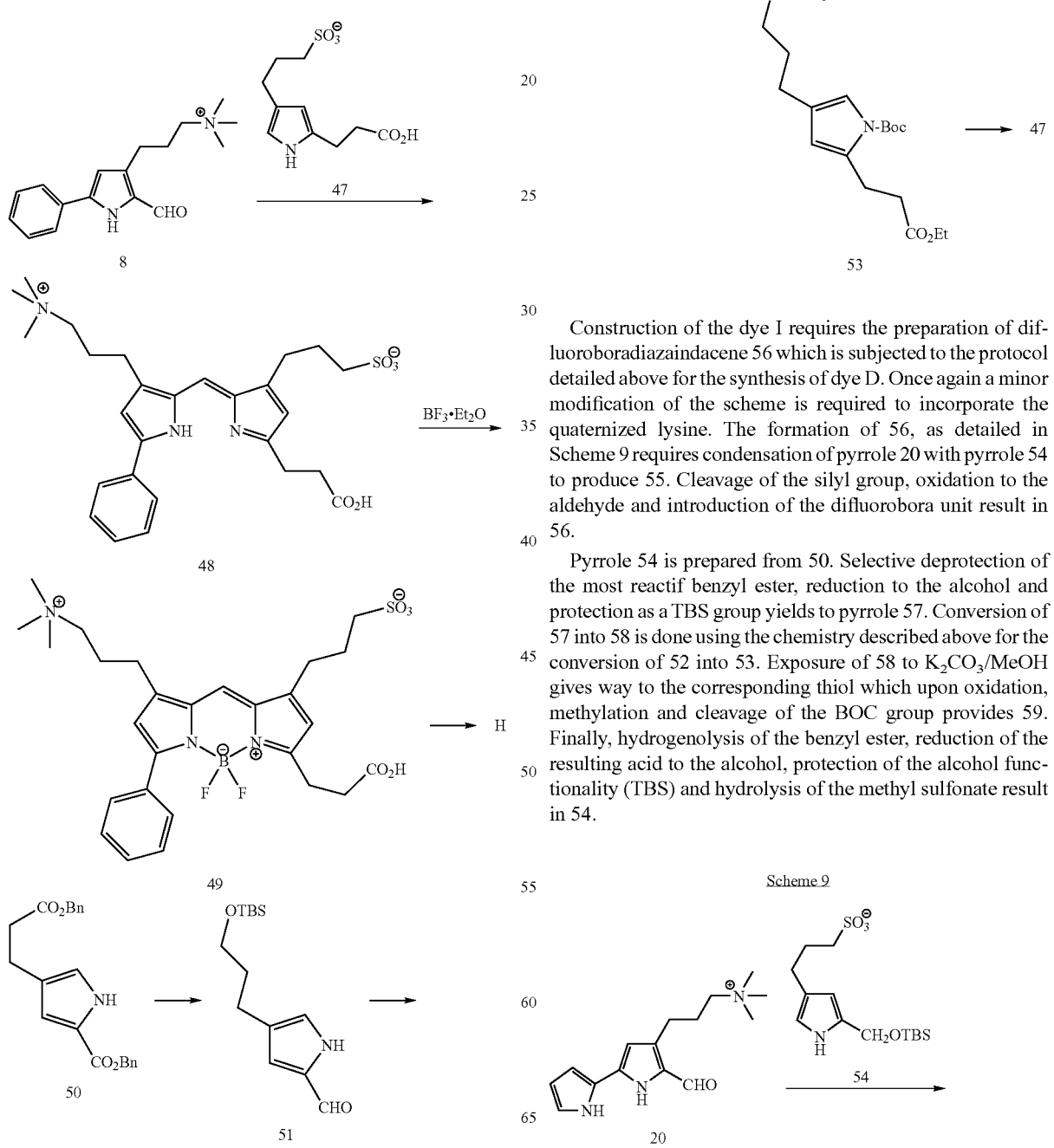

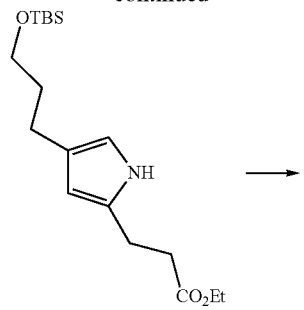

Construction of the dye I requires the preparation of difluoroboradiazaindacene 56 which is subjected to the protocol detailed above for the synthesis of dye D. Once again a minor modification of the scheme is required to incorporate the quaternized lysine. The formation of 56, as detailed in Scheme 9 requires condensation of pyrrole 20 with pyrrole 54 to produce 55. Cleavage of the silyl group, oxidation to the aldehyde and introduction of the difluorobora unit result in 56.

Pyrrole 54 is prepared from 50. Selective deprotection of the most reactif benzyl ester, reduction to the alcohol and protection as a TBS group yields to pyrrole 57. Conversion of 57 into 58 is done using the chemistry described above for the conversion of 52 into 53. Exposure of 58 to $K_2CO_3$/MeOH gives way to the corresponding thiol which upon oxidation, methylation and cleavage of the BOC group provides 59. Finally, hydrogenolysis of the benzyl ester, reduction of the resulting acid to the alcohol, protection of the alcohol functionality (TBS) and hydrolysis of the methyl sulfonate result in 54.

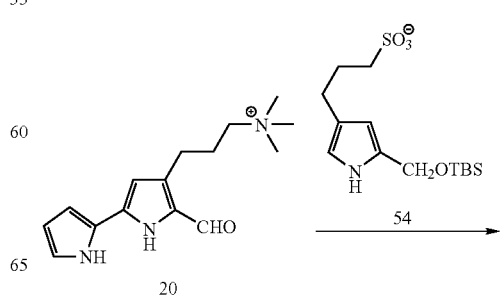

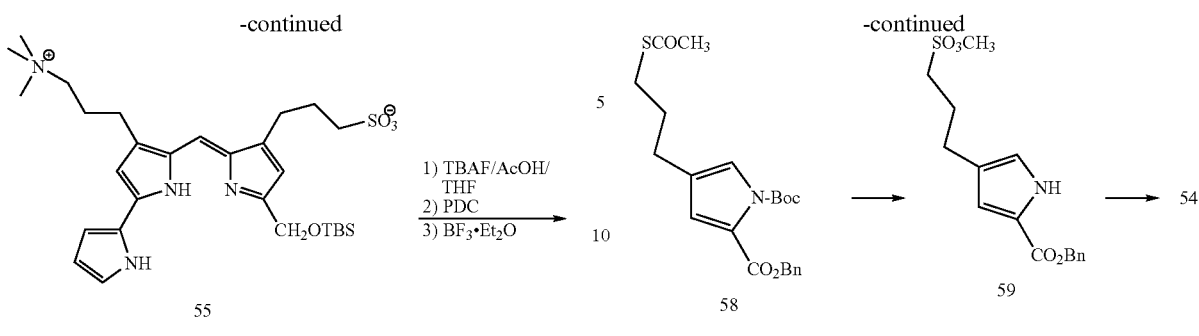

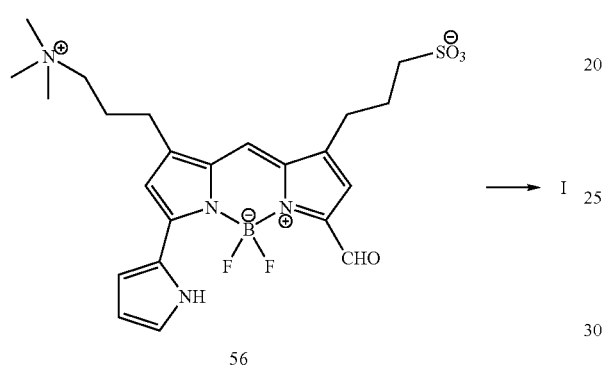

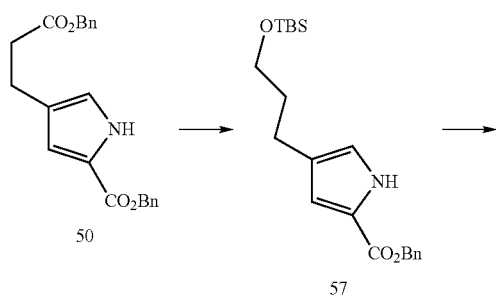

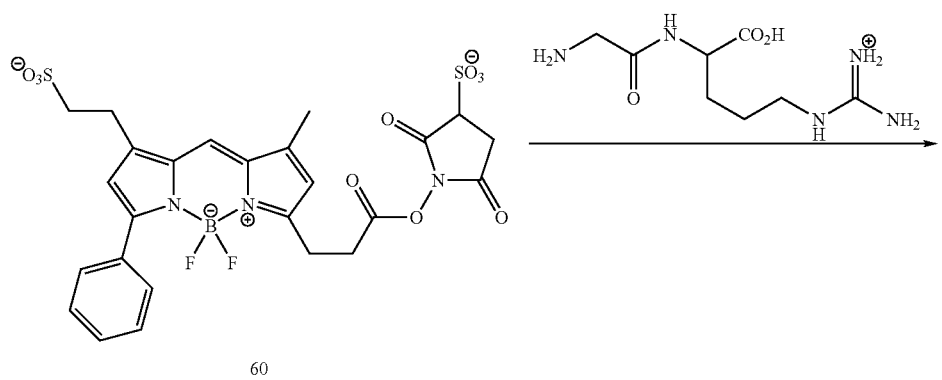

EXAMPLE 2

Synthesis of Dyes A2-I2

This examples sets forth an example of synthesis for dyes A2-12 (FIGS. 9A and 9B)

The series A2-I2 presents 2 major differences with respect to the series A-I shown in Example 1. These two modifications are exemplified with the synthesis of A2 in Scheme 10. The first one is the replacement of the cysteic acid residue with arginine in the conversion of 60 to 61. Using arginine in place of cysteic acid in the various synthetic routes will easily take care of this modification. The second difference is in the replacement of the side chain containing the quaternary ammonium group with a sulfonate. This can be carried out by using isopropyl diethylphosphorylmethanesulfonate in a Horner-Wadsworth-Emmons coupling step as in the conversion of 6 into 62 (Carretero J. C., Demillequand M. and Ghosez L, Synthesis of alpha, beta-unsaturated sulphonates via the Wittig-Horner reaction; *Tetrahedron* Vol. 43,No. 21, pp. 5125-5134, 1987.). The newly introduced ethyl sulfonate is then deprotected to the sulfonate following the formylation step to generate 63. 63 is converted into 60 using the procedure described for the synthesis of A. These steps can be generalized to the synthetic routes of dyes B2-I2.

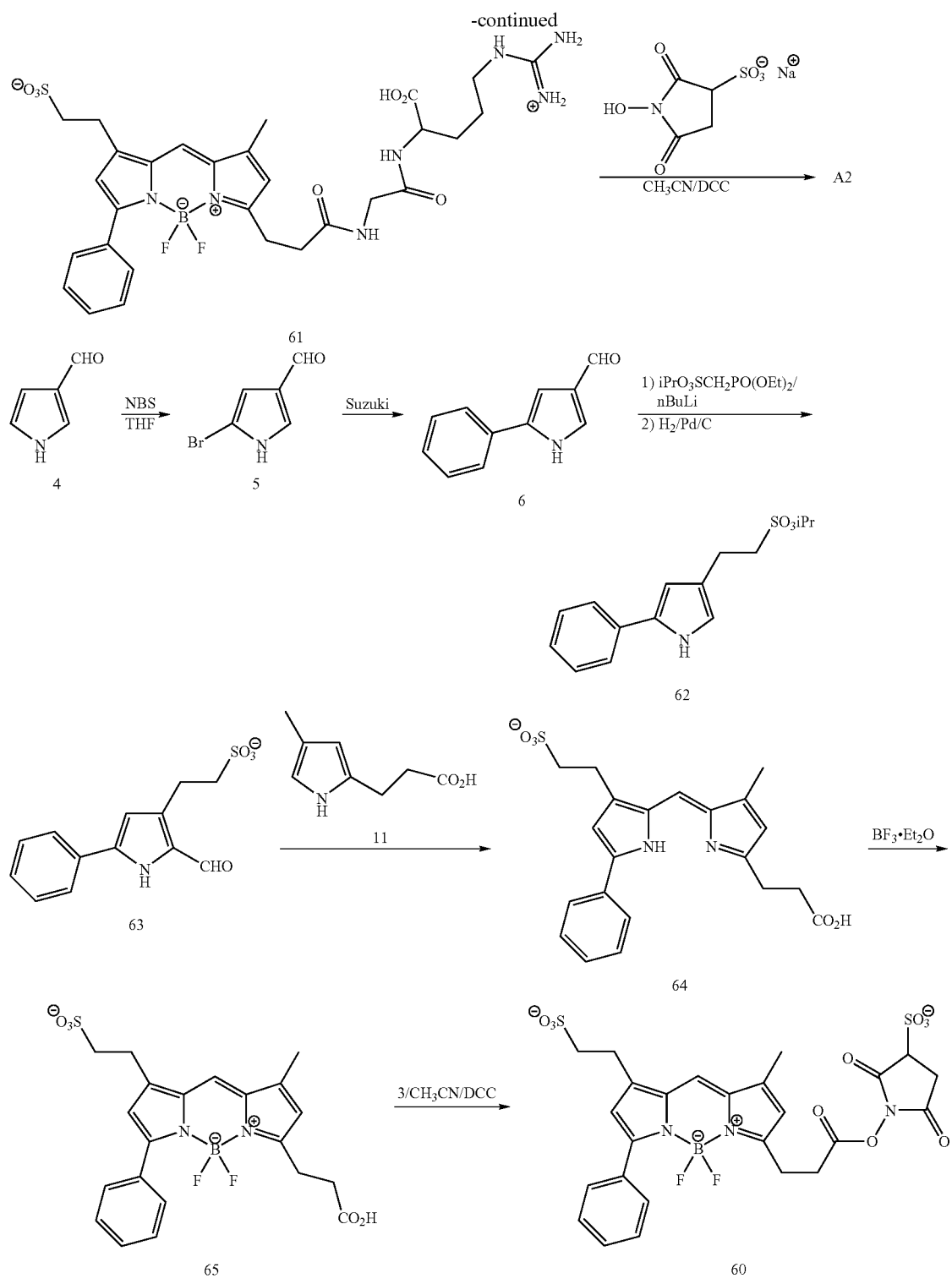

In addition to the two previously described variations, the dyes H2 and I2 present a third modification with respect to dyes H and I: a shortening of the sulfonate side chain from a three to a two carbon tether. This adjustment is made by substituting pyrroles 68 and 71 to pyrroles 47 and 54 respectively in the synthesess of H and I. The syntheses of fragments 68 and 71 are illustrated in Scheme 11.

The synthesis of Pyrrole 68 starts with the known pyrrole-3-carboxaldehyde 4. (Bray, B. L., et al., "N-(Triisopropylsilyl)pyrrole. A Progenitor "Par Excellence" of 3-Substituted Pyrroles", *J. Organic Chem.* 1990, 55(26),6317-6328) Coupling of 4 with the known isopropyl diethylphosphorylmethanesulfonate (Carretero J, et al.; *Tetrahedron* Vol. 43,No. 21, pp. 5125-5134, 1987) and subsequent catalytic hydrogenation of the resulting olefin leads to intermediate 66. Formylation of 66 into 67 is carried out under the Vilsmeier-Haack conditions. At this point the stage is set for the Doebner coupling of formyl pyrrole 67 with mono ethyl malonate which after hydrogenolysis and hydrolysis of the esters will generate 68.

The synthesis of 71 starts with the known ester 69. ("Sambrotta, L., et al., "Synthesis of 8-Demethyl-8-Formyl Protoporphyrin IX and of 8-Demethyl Protoporphyrin IX", *Tetrahedron* 1989, 45, 6645-6652) Treatment of 69 under the conditions described above leads to ester 70, which is subsequently reduced to the corresponding alcohol, hydrolysed and selectively reprotected to yield 71.

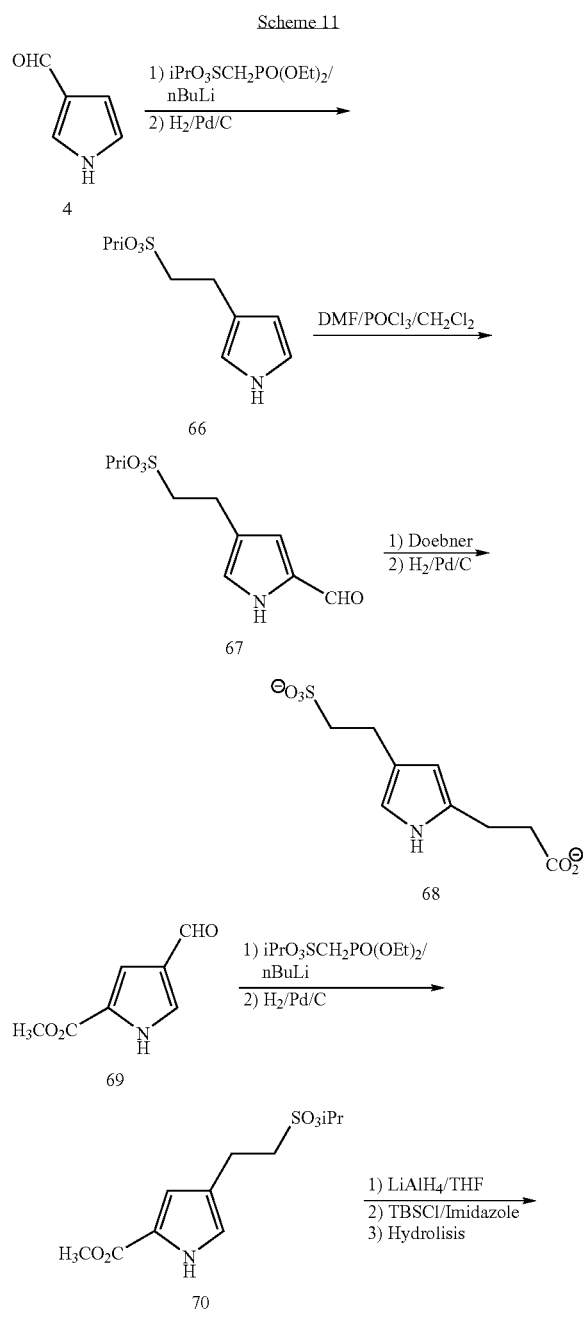

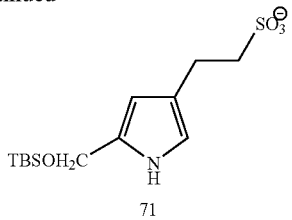

EXAMPLE 3

Synthesis of Dyes A3-I3

This Examples Sets Forth an Example of Synthesis for Dyes A3-I3 (FIGS. 10A and 10B)

Dyes A3-I3 are synthesized as described in Example 2 for Dyes A2-I2 except that the arginine residue is substituted with a trimethylated lysine, using trimethylated lysine in place of arginine in the various synthetic routes. Trimethyllysine has an advantage for some applications that it is not cleaved by trypsin, whereas arginine is, in general, cleaved by trypsin. Arginine is not a problem with many applications of the zwitterionic dyes described, where the dyes are removed after protein separation and quantitation, but before protease digestion for mass spectral analysis.

Additional examples of synthesis for dyes A-I, A2-I2 and A3-I3 are found in U.S. patent application Ser. No. 10/623,447, hereby incorporated by reference.

EXAMPLE 4

Evaluation and Optimization of Labeling of Target Proteins from Different Types of Samples The sensitivity of labeling to pH, buffer type, and common salts in the reaction medium is tested for different sample types, using parallel readout of the results of different conditions on 1D electrophoresis and quantitation of labeled proteins with laser excited fluorescent gel scanning. Phosphate buffer is used near pH 7.4, a phosphate/borate mixture near pH 8, and borate near pH 8.5 or 9.0. Tris buffers or other buffers with potentially reactive amines must be avoided. The best ratio of labeling to hydrolysis is near pH 8.5, unless SDS or other anionic detergent is used to solubilize the proteins and then a somewhat higher pH is favorable. The labeling rate of amino groups with the sulfo-succinamidyl or succinamidyl groups increases with pH, however at too high a pH the succinamidyl group hydrolyzes. Labeling kinetics are measured by quenching the labeling reactions at different times with excess glycine, hydroxylamine or low pH. Possible enhancement of labeling can be assessed for different samples in the presence of the detergents, urea, and thiourea used for IEF, using, 1D SDS gels and fluorescence emission as the readout.

After favorable pH and labeling times are established for samples from different organisms or tissues, experiments may be carried out to vary the optical labeling molecule/protein ratio during labeling. The approximate number of optical labeling molecules per labeled protein and the relative fluorescence of the optical labeling molecules on different labeled proteins is determined, using on-line fluorescence and absorbance detection in HPLC gel filtration experiments. The HPLC gel filtration separates the free optical labeling molecule from the labeled proteins. Proteins used in such studies can be chosen to allow separation based on size by HPLC gel filtration. The amount of each protein added to the reaction mixture is known and the amount of 280 absorbance observed from the known amount of protein is determined in the HPLC on unlabeled and labeled samples. The stoichiometry of the optical labeling molecule to protein is determined from absorbance measurements of the dye moiety of the optical labeling on each protein peak and the relative extinction coefficients of the protein and the dye moiety. Fluorescence/absorbance ratios on each protein peak, relative to the free optical labeling molecule, allows detection of fluorescence quenching by the protein or by excessive numbers of optical labeling molecule/protein.

Such experiments also allow determination of the ratio of protein labeling to optical labeling molecule hydrolysis under different conditions, as it is desirable to minimize the remaining free optical labeling molecule for improved detection of low molecular weight proteins. The ratio of hydrolyzed and unreacted optical labeling molecule are determined on the free optical labeling molecule fraction by RP-HPLC. Too high an optical labeling molecule concentration during labeling might produce some dye fluorescence quenching by excessive protein labeling or produce inactive optical labeling molecule dimers or even higher multimers from these particular optical labeling molecule. If optical labeling molecule dimerization occurs, it will be controlled by variation of labeling conditions. If necessary, more sterically-hindered tertiary amine groups (such as a t-butyl) can be substituted for the titratable group in the synthesis of the dye.

The strength of on-gel fluorescent signals is measured as a function of the number of optical labeling molecules per protein using gel filtration analysis of aliquots of the samples, where the labeling stoichiometry has been determined by gel filtration, as described above, it is not anticipated that the quenching of fluorescent signals will differ much in solution vs. in gels, as a function of the number of optical labeling molecule/protein, except at the highest protein loadings on gels where fluorescence quenching may be observed. Such experiments establish the range of linearity of fluorescence signals and the dynamic range of detection of optical labeling molecule-labeled proteins on gels. Any differences in labeling of proteins in specific mixtures of proteins with different members of the optical labeling molecule sets, or families, can be detected by splitting identical protein mixtures, labeling each half of the sample with different optical labeling molecule, mixing the samples and detecting the fluorescence ratios for each band on 2D gels. Any departure from a constant ratio of fluorescence signals across bands on the gel would indicate differences in labeling, but this is not expected to be significant. If significant optical labeling molecule-dependent labeling is seen with some proteins, a labeling reversal experiment should be done routinely to allow correction for this effect in practical functional proteomics experiments.

The stability of the dye binding to the labeled proteins can be determined by centrifugal filtration to concentrate each protein peak from HPLC gel filtration, incubation of the purified, labeled proteins for various times (in the presence of sodium azide and protease inhibitors) and measuring any loss of labeling by rerunning on gel filtration. The UV-reversible linkages in some of the compounds require protection from fluorescent light for highest stability, and sample tubes must be foil wrapped and manipulated under dim incandescent light.

EXAMPLE 5

Effect of Optical Labeling Molecule on Protein Solubility and Two-Dimensional Gel Electrophoresis Mobility The effect of the optical labeling molecule on protein solubility and 2DE mobility is assessed using fluorescent signals and radioactive labeling of standard proteins. The solubilities of labeled proteins can be assessed by running them on IEF (isoelectric focusing) and 2D (two-dimensional) electrophoresis to assess any changes of retention of proteins on the IEF strips before and after labeling. Retention of protein on the IEF strips and poor transfer into the second dimension is often found in 2D electrophoresis if sample loadings are too high or if solubilization conditions are inadequate. Fluorescent signals of labeled proteins retained on IEF strips provide semi-quantitative measurements of limited solubility since the strong signals can exceed the linear range. The use of the optical labeling molecules of the invention will lead to substantial protein solubility increases compared to the unlabeled protein samples. To verify this phenomenon, radioactively labeled standard proteins and complex mixtures of proteins from cells are used for assessment of any labeling induced gel mobility shifts (see below) and these same radioactive proteins will be useful for quantitative solubility assessments. Phosphorimaging of the 2DE gels, and any protein residues on the IEF strips, provides a quantitative measure of insoluble proteins remaining on the LEE strips, relative to the radioactivity on the second dimension.

Two methods of radioactive labeling of the standard proteins are used. N-acetyl labeling with tritiated acetic anhydride at near neutral pH largely couple to N-terminal groups. Excess acetic anhydride will be removed by HPLC gel filtration, followed by fluorescent dye labeling of the epsilon amino groups of lysine at elevated pH (e.g. 8.5). An alternative method of radioactive labeling first reduces protein sulfhydryl groups with tributylphosphine (TBP), tricarboxyethyl phosphine (TCEP), or other trisubstituted phosphine compound. The sulfhydryl groups are then labeled with radioactive iodoacetamide and the amino groups labeled with dyes.

2D gels are run on the radioactively tagged and fluorescently labeled proteins after low (substoichiometric), medium (one or two optical labeling molecules per protein) and high optical labeling molecules labeling (many optical labeling molecules per protein). Gels are scanned for fluorescence and the location of radioactive spots will be measured by phosphorimaging on the same BioRadFX Fluorescent Gel Scanner and Phosphoimager. The radioactivity shows the position of proteins that are not labeled, as well as the labeled proteins. Thus, any optical labeling molecule-induced shifts in protein patterns is detected and monitored by comparing radioactivity patterns to fluorescence patterns. An expected reduction of shifts is assessed using the optical labeling molecules with titratable groups. The dyes with titratable amine groups are especially valuable in the high pH range from 10-12. Commercial IEF strips are now available from Pharmacia up to pH=11 and if strips up to pH=12 are not commercially available, the needed strips may be prepared following publications of the Gorg lab in Munich (Gorg, A., et al., (1999) Recent developments in two-dimensional gel electrophoresis with immobilized pH gradients: wide pH gradients up to pH 12, longer separation distances and simplified procedures, *Electrophoresis* 20: 712-717; Gorg, A. (1999) IPG-Dalt of very alkaline proteins, *Methods Mol. Biol.* 112, 197-209; Gorg, A., et al., (2000) The current state of two-dimensional electrophoresis with immobilized pH gradients, *Electrophoresis* 21, 1037-1053, each of which is hereby expressly incorporated by reference). The larger the multiplicity of optical labeling molecules labeling on target proteins the larger the fluorescent signals (up to the point where fluorescence quenching becomes a problem). Thus, the labeling conditions can be optimized for maximum sensitivity consistent with acceptable mobility shifts for mixtures of proteins from particular organisms or tissues.

With two (or multiple) color ratio recording of fluorescent signals, the information content as to which proteins are changing in level with physiological stimulus is insensitive to optical labeling molecule-induced shifts as long as the shifts are the same or very similar for the different dyes. However, increased complexity or spot distortion would occur if labeling shifted the gel mobility with increasing number of optical labeling molecules bound/protein. If labeled protein spots are resolved from other proteins then the fluorescence ratios will still contain reliable information on the relative expression of proteins under different physiological conditions. Thus, any significant shifts with labeling will favor increased reliance on narrow pH range IEF gels to spread proteins over 1 or 2 unit pH range. Optical labeling molecule-induced shifts are not expected to be very large due to the modest resolution of 2D gels. A tradeoff between minimum complexity and lower sensitivity with sub-stoichiometric labeling, to possibly more spot complexity and highest sensitivity with high optical labeling molecule labeling will be under experimental control.

EXAMPLE 6

Testing of the Protein Pre-Labeling Methods on Standard Proteins

A very large range of protein abundance/concentration is found in cells, tissues and bodily fluids. Increased dynamic range of protein measurement can be obtained by labeling samples at more than one level of dye multiplicity and scanning gels at several different photomultiplier amplifications. After the desirable conditions for different multiplicity of optical labeling molecule labeling are established for particular protein mixtures, the detection limit and linearity of the fluorescence signal vs. amount of protein loading can be determined. These experiments can be carried out at low labeling multiplicity, medium multiplicity and high multiplicity of optical labeling molecule labeling that is found to be useful in prior experiments and can also determine the dynamic range for the method and the scanner in practice. A dilution series of standard proteins labeled with the optical labeling molecules is made and the different dilutions run on different lanes of ID gels.

Similar experiments can be carried out with two and three or several different optical labeling molecules using identical standard protein mixtures. In multiple color optical labeling molecule experiments, dye cross talk and multiplex sensitivity is determined, using constant amounts of one or two of the labeled protein mixtures (at a relatively high level) and varying the amount of proteins labeled with a second or third optical labeling molecule in steps from the detection limit to very high levels. The degree of crosstalk between the two main groups of optical labeling molecule investigated is extremely low due to the essentially non-existent direct excitation of the partner dyes by the lasers to be used. Double-label pairs with minimum cross-talk are dyes A, C, E, or H (excited with the 488 nm laser)-paired with B, D, F or I (excited with the 633 nm laser).

Dye G can be used as a third optical labeling molecule and excited with the 532 mm laser, with only modest cross talk expected with the other dyes. The degree of crosstalk is determined by comparing gels from a standard curve of protein fluorescence on a dilution series, using a single optical labeling molecule, to the same dilution series in the presence of a constant, high level of proteins labeled with a second optical labeling molecule. Any preference of optical labeling molecule for different proteins is determined by labeling protein mixtures separately with the different optical labeling molecules, mixing the two or three different labeled proteins in the same amounts, running electrophoretic separations and determining the fluorescence color ratios.

EXAMPLE 7

Recovery of Proteins from 2D Gels and Efficiency of Removal of Optical Labeling Molecule The recovery of proteins from 2D gels and efficiency of removal of the optical labeling molecule is assessed and optimized using radioactively labeled proteins with and without the optical labeling molecule. Initial experiments are carried out in aqueous solution on glycine-quenched dyes to test the amount and type of UV irradiation needed to remove the reversible linker efficiently, using RP-FPLC to analyze the products. Known amounts of labeled standard proteins are run in duplicates. Fluorescence and phosphoimager scanning can be used to confirm the dilution series. Consistent-sized gel circles are punched out of the gel, frozen in liquid nitrogen and the gel pieces powdered with a stainless steel rod in microfuge tubes. One of the duplicate samples is counted for radioactivity and the other is freeze-dried and then rehydrated in a buffer containing Promega autolysis-resistant trypsin, (+/−TCEP and IAA to enhance recovery of cysteine-containing peptides). Dye labeled and control samples are treated with UV (365 nm mercury lamp) to remove the reversible optical label molecule linkage. After incubation (24-48 hours) gel pieces are extracted with 50% acetonitrile and the supernatant harvested by centrifugal filtration using a filter that is resistant to acetonitrile (e.g. Millipore Biomax) to retain the gel fragments. The extraction is repeated once or more with acetonitrile and the extracts are counted to determine the recovery of peptide radioactivity. Control proteins with no labels are hydrolyzed in solution with trypsin in $H2O^{18}$ to mark the trypsin cleavage sites with $0^{18}$ substitution (Shevchenko, A. and Shevchenko, A. (2001) Evaluation of the Efficiency of 1n-gel Digestion of Proteins by Peptide Isotopic Labeling and MALDI Mass Spectrometry. *Anal. Biochem* 296, 279-283, hereby expressly incorporated by reference). Aliquots of the $0^{18}$-labeled peptides are added to the extraction steps and the ratios of $0^{16}$ peptides to $0^{18}$ peptides monitored by mass spectrometry to determine the percentage of recovery of peptides from the protein. The peptides are run on MALDI and ESI/MS/MS to determine peptide recovery +/−UV treatment to remove the dye labels, using $0^{18}$ internal standards. Standard acrylamide gels and meltable Proto-Preps system gels (National Diagnostics) will be compared. Protocols for efficient protein digestion and peptide recovery will be optimized to maximize the conditions for effective protein identification using mass spectral analysis. 0.1% octyl glucoside may be included to improve recovery of tryptic peptides from in-gel digests (Mann, M., et al., (2001)

Analysis of proteins and proteomes by mass spectrometry, Annu. Rev. Biochem. 10, 437-473, hereby expressly incorporated by reference).

EXAMPLE 8

Testing of the Optical Labeling Molecules on Total Bacterial Proteins

The properties of the optical labeling molecules i can be evaluated on the complex protein mixture in the total protein complement of an organism. For example, the hyperthermophilic archeabacterium, *Sulfolobus solfararicus*, can be use to evaluate the optical labeling molecules.

An advantage to the use of a microorganism for testing and evaluation of proteomic methodology is that all the proteins in the microorganisms can easily be radioactively labeled, using radioactive sulfur$^{-35}$ in the growth medium. Radioactive labeling provides tremendous advantages for assessment of protein recovery from gels and any label-induced gel mobility shifts. Essentially the same techniques are used for analysis of the total *Sulfolobus* proteins as was described above. *Sulfolobus* provides a wide range (about 3,316 proteins in the geonome) of proteins with a much greater variety of characteristics, than possessed by standard protein mixtures (discussed in earlier sections). In particular, there is the opportunity to discover any dye-specific labeling preferences in the wide range of *Sulfolobus* proteins using simple dye cross-over labeling experiments. Comparison of radioactivity and dye labeling are used to detect any dye labeling-induced shifts on complex protein mixtures from *Sulfolobus*. Protein spots are cut out of the gel, the dye label is removed by UV irradiation (365 or 308 nm), the proteins digested with trypsin in the presence of octyl glucoside to enhance recovery (Katayama, H., et al., (2001) Improvement of in-gel digestion protocol for peptide mass fingerprinting by matrix-assisted laser desorption/ionization time-of-flight mass spectrometry, *Rapid Comm. Mass Spectrom.* 15, 1416-1421, hereby expressly incorporated by reference), peptides are extracted and submitted to mass spectral analysis using the best procedures available (Gygi, S. P. and Aebersold, R. (2000) Mass spectrometry and proteomics, *Curr. Opin. Chem. Biol.* 4: 489-494; Loo, J. A., et al., (1999) High sensitivity mass spectrometric methods for obtaining intact molecular weights from gel-separated proteins, *Electrophoresis*, 20, 743-748, Kraft, P. et al., (2001) Mass spectrometric analysis of cyanogen bromide fragments of integral membrane proteins at the picomole level: application to rhodopsin, *Anal. Biochem.* 292, 76-86, each of which is hereby expressly incorporated by reference). For example, nano-spray and tandem mass spectral techniques can be used as a method to identify proteins and post-translational modifications.

EXAMPLE 9

Multiplex Detection of Phosphorylation

Phosphorylation is one of the most common post-translational modifications in cellular regulation, but because of the labile nature of this modification, phosphorylation is difficult to detect by mass spectrometry. Some of the Trk receptor isoforms are phosphorylated and there is evidence that several signaling cascades are activated (Patapoutian A, and Reichardt L F., Trk receptors: mediators of neurotrophin action, *Curr Opin Neurobiol.* 2001 Jun. 11 (3):272-80, hereby expressly incorporated by reference). In addition to the methods of detecting the presence or absence of proteins, or quantity of protein, with fluorescence detection, multiplex detection of phosphorylation can be performed with all the proteins on the same sample as described previously and below.

The dorsal root ganglia (DRG) cells are cultured as described (Garner, A. S, and Large, T. H. (1994) Isoforms of the avian TrkC receptor: a novel kinase insertion dissociates transformation and process outgrowth from survival, *Neuron* 13, 457-472), unstimulated cells are labeled with $^{33}$P phosphate and growth factor stimulated cells are labeled with $^{32}$P phosphate. After suitable incubation the two cell samples are extracted. The $^{33}$P-labeled extracts are reacted with a first optical labeling molecule and the $^{32}$P-labeled extracts are reacted with a second different optical labeling molecule. The first and the second optical labeling molecules are chosen from the same set of optical labeling molecules so that the optical signal is different but the physical characteristics are similar. The labeled extracts will be mixed together, run on 2D gels and laser scanned for the protein expression ratios between the stimulated and unstimulated cells. In addition, two phosphoimager image plates will be exposed simultaneously on two sides of the same gel, one phosphoimager plate directly on the gel and the other having a I mil thickness of copper foil in front of tine phosphoimager plate (Bossinger, J., et al., (1979) Quantitative analysis of two-dimensional electrophoretograms, *J. Biol. Chem.*, 254, 7986-7998; Johnston, R. F., et al., (1990) Autoradiography using storage phosphor technology, *Electrophoresis*, 11, 355-360; Pickett, S. C., et al., (1991) Quantitative double-label autoradiography using storage phosphor imaging, *Molecular Dynamics Application Note*). The directly exposed P1 plate registers the sum of both isotopes, whereas the copper foil-filtered phosphoimager image almost entirely blocks the $^{31}$P, whereas barely attenuating the signals from the $^{32}$P. The results of these studies will be compared to direct dye staining of the serine and threonine phosphorylated proteins using beta-elimination of the phosphates by base treatment of the gels after fluorescent and phosphoimager scanning or after transfer of proteins to PVDF membranes and staining of the beta-eliminated sites with high sensitivity fluorescent dyes, as shown in FIGS. 7A and 7B and discussed above.

Thus, the multiplex methods of the invention can be extended for with simultaneous monitoring of changes in phosphorylation, as well as the changes in the level and post-translational modification of the proteins associated with function.

We claim:

1. An optical labeling molecule for labeling a target analyte comprising:
   a. a boron difluoride diaza-indacene-propionic acid (BODIPY) zwitterionic dye moiety comprising at least one positive or at least one negative charge moiety added to obtain a net neutral charge, wherein the positive charge moiety is selected from a group consisting of a quaternary ammonium group and a guanidinium group, wherein the positive charge moiety is not titratable between the pH of 3-12, and wherein the negative charge moiety is selected from the group consisting of a sulfonate group and a sulfate group, wherein the negative charge moiety is not titratable between the pH of 3-12;
   b. a functional linker moiety; and
   c. a titratable group moiety, wherein the titratable group is a tertiary amine which closely approximates the pK of the group removed from the target analyte by reaction with the functional linker.

2. The optical labeling molecule of claim 1, wherein the zwitterionic dye moiety comprises a chromophore responsible for a detectable optical signal.

3. The optical labeling molecule of claim 1, wherein the said positive and said negative charge moieties are added to a neutral dye or a charged dye to produce a zwitterionic dye molecule.

4. The optical labeling molecule of claim 1, wherein the zwitterionic dye moiety comprises at least one quaternary ammonium group and at least one sulfonate group.

5. The optical labeling molecule of claim 1, wherein the zwitterionic dye moiety comprises at least two quaternary ammonium groups or at least two guanidinium groups and at least two sulfonate groups.

6. The optical labeling molecule of claim 1, further comprising a cleavable moiety selected from a group consisting of a chemical moiety, a photocleavable moiety and an enzymatically cleavable moiety.

7. The optical labeling molecule of claim 6, wherein the photocleavable moiety is selected from a group consisting of an O-nitrobenzylic compound, a benzoin moiety, and a nitrophenylcarbamate ester.

8. The optical labeling molecule of claim 1, further comprising a second label, wherein the second label comprises a light stable isotope or a heavy stable isotope.

9. The optical labeling molecule of claim 1, wherein the linker moiety is an amino group reactive linker selected from the group consisting of an imidoester, a N-hydroxysuccinimidyl ester, an isothiocyanate, a sulfosuccinimidyl group, an aldehyde, and a sulfonylchloride-reactive linker and a sulfhydryl-reactive linker.

10. The optical labeling molecule of claim 9, wherein the sulfhydryl-reactive linker is selected from the group consisting of a maleimide, an iodoacetamide, an alkyl bromide and a benzoxidiazole.

11. The optical labeling molecule of claim 1, wherein the dye moiety further comprising at least one added negative charge moiety selected from a sulfonate group or a sulfate group and at least one added positive charge moiety selected from a group consisting of a quaternary ammonium group, a guanidinium group and a positive charge group.

12. The optical labeling molecule of claim 1, wherein the labeling molecule has the general structure:
wherein ZD is the zwitterionic dye moiety, T is the titratable moiety, and A is the linker moiety.

13. The optical labeling molecule of claim 1, wherein the labeling molecule has the general structure:
ZD-T-A-
wherein ZD is the zwitterionic dye moiety, T is the titratable moiety, and A is the linker moiety.

14. The optical labeling molecule of claim 1, wherein the labeling molecule has the general structure:
T-ZD-C-A- or ZD-T-C-A
wherein ZD is the zwitterionic dye moiety, T is the titratable moiety, C is the cleavable moiety, and A is the linker moiety.

15. The optical labeling molecule of claim 1, wherein the labeling molecule has the general structure:
T-ZD-C-I-A-
wherein ZD is the zwitterionic dye moiety, T is the titratable moiety, C is the cleavable moiety, I is the stable isotope moiety, and A is the linker moiety.

16. The optical labeling molecule of claim 1, wherein the labeling molecule has the general structure:
ZD-T-C-I-A-
wherein ZD is the zwitterionic dye moiety, T is the titratable moiety, C is the cleavable moiety, I is the stable isotope moiety, and A is the linker moiety.

17. The optical labeling molecule of claim 16, further comprising:
(d) a photocleavable moiety wherein such photocleavable moiety is an O-nitrobenzylic compound.

18. The optical labeling molecule of claim 1 comprising:
a functional linker moiety wherein such linker is a N-hydroxysuccinimidyl ester.

19. A cellular component selected from the group consisting of proteins, carbohydrates, lipids, and nucleic acids covalently attached to the optical labeling molecule of claim 1.

20. The cellular component of claim 19, wherein the said component is a protein.

21. The cellular component of claim 19, wherein the said component is a carbohydrate.

22. The optical labeling molecule of claim 1, prepared by
(a) providing a boron difluoride diaza-indacene-propionic acid (BODIPY) dye moiety comprising one or more positive or one or more negative charge moieties;
(b) adding at least one positive charge moiety selected from the group consisting of a quaternary ammonium group, a guanidinium group and a positive charge group, wherein the positive charge moiety is not titratable between the pH of 3-I2, or at least one negative charge moiety selected from a group consisting of a sulfonate group and a sulfate group, wherein the negative charge group is not titratable between the pH of 3-I2 to form a zwitterionic dye moiety;
(c) contacting the zwitterionic dye moiety with a titratable group moiety; and
(d) contacting the product from step (c) with a functional linker moiety to provide a optical labeling molecule comprising a zwitterionic dye moiety characterized by a net neutral charge when bound to the target analyte.

23. The optical labeling molecule of claim 22, wherein the zwitterionic dye moiety is a fluorescent dye.

24. The optical labeling molecule having formula (I):

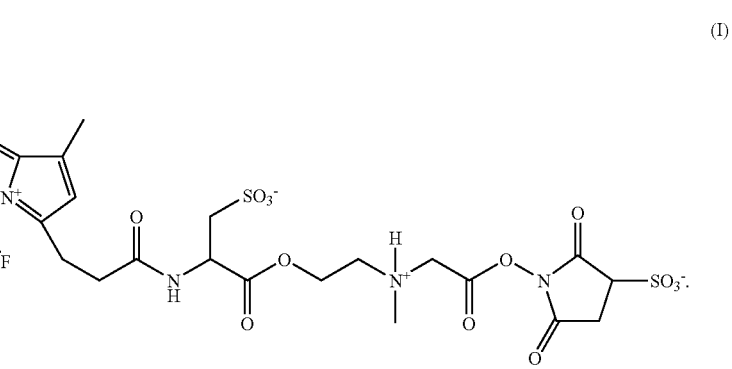

(I)

25. The optical labeling molecule which is selected from the group consisting of:
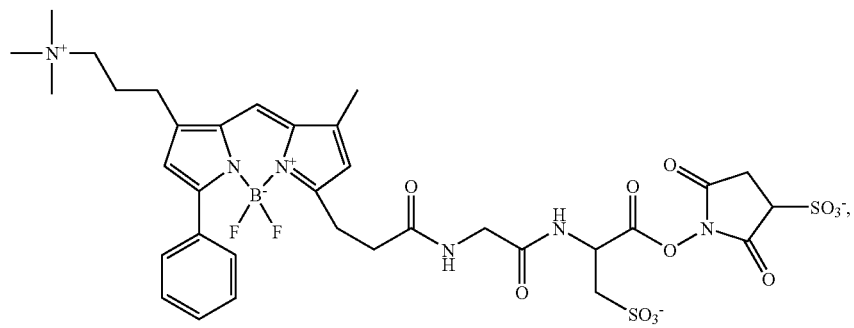
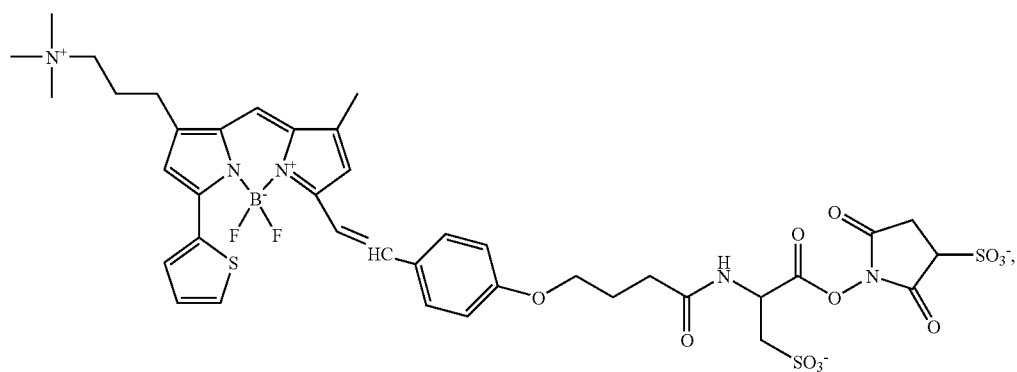
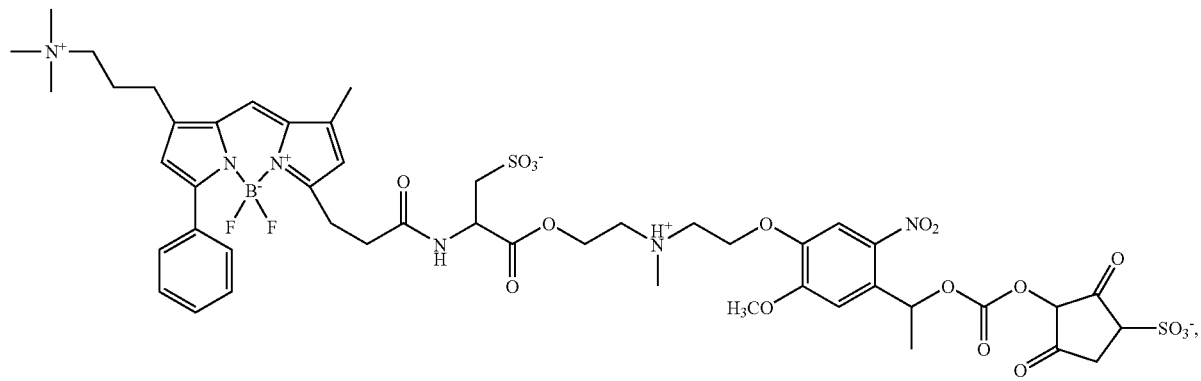
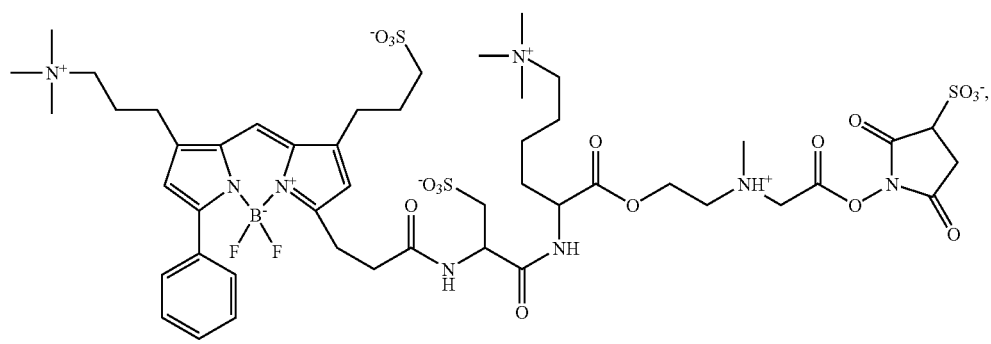

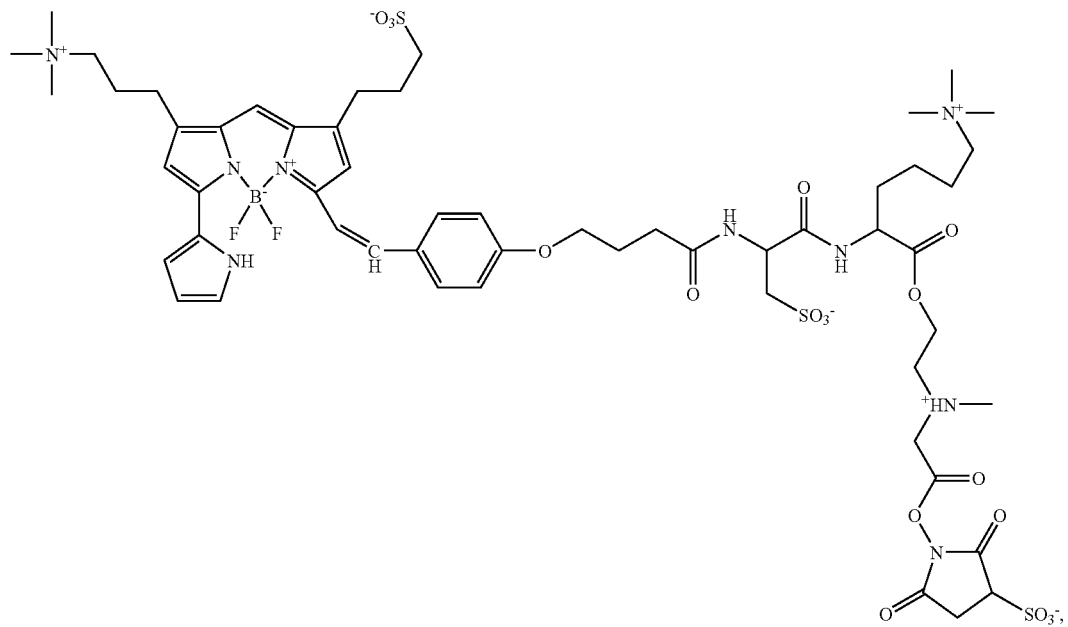
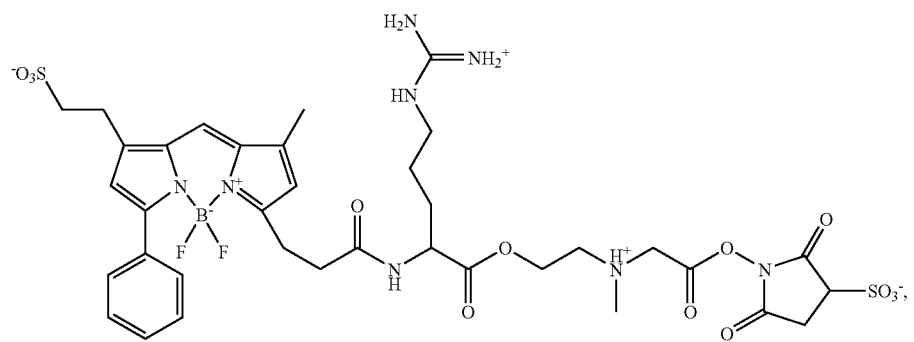
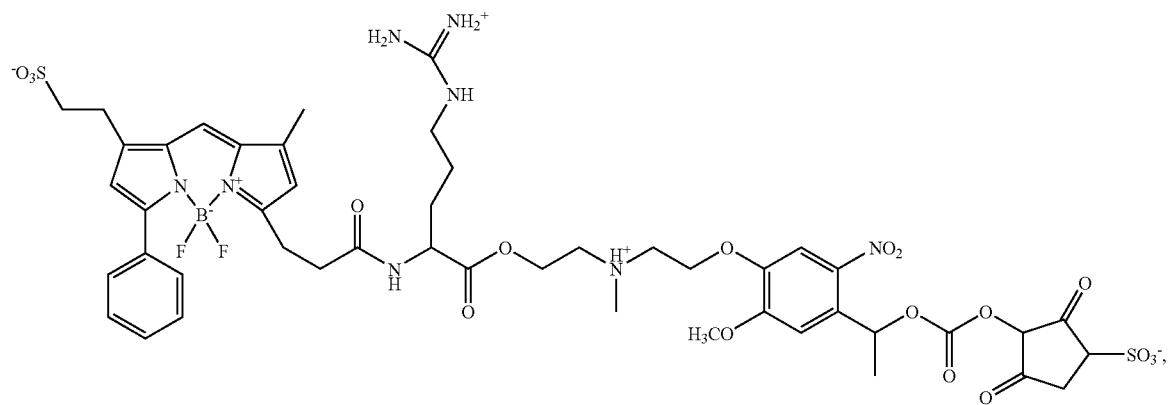

-continued
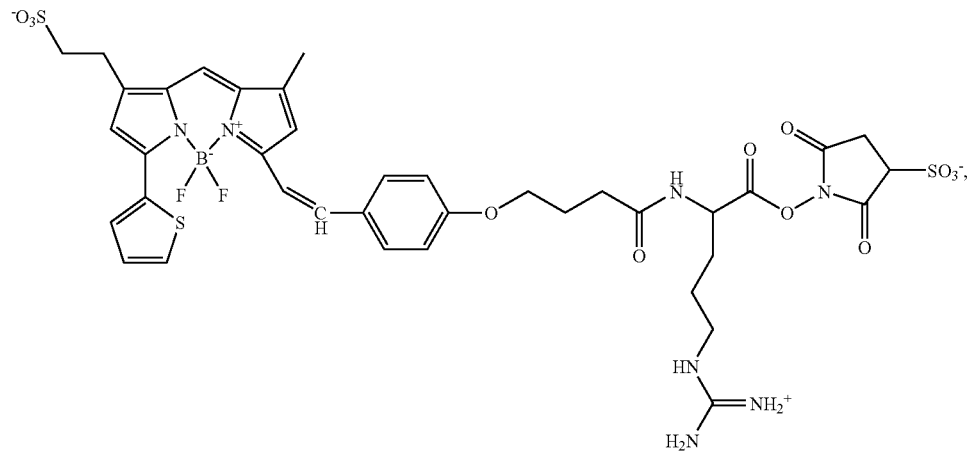
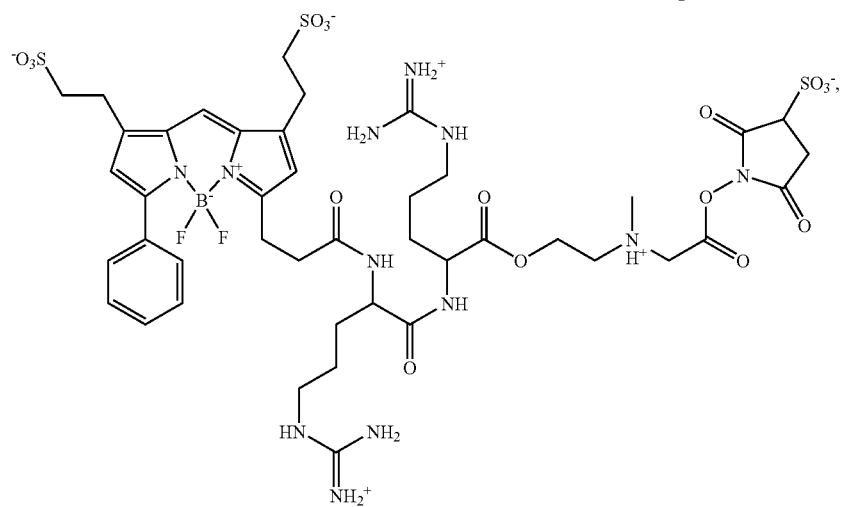
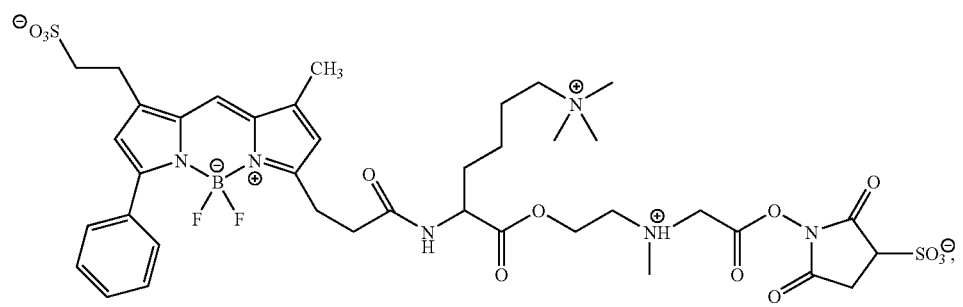
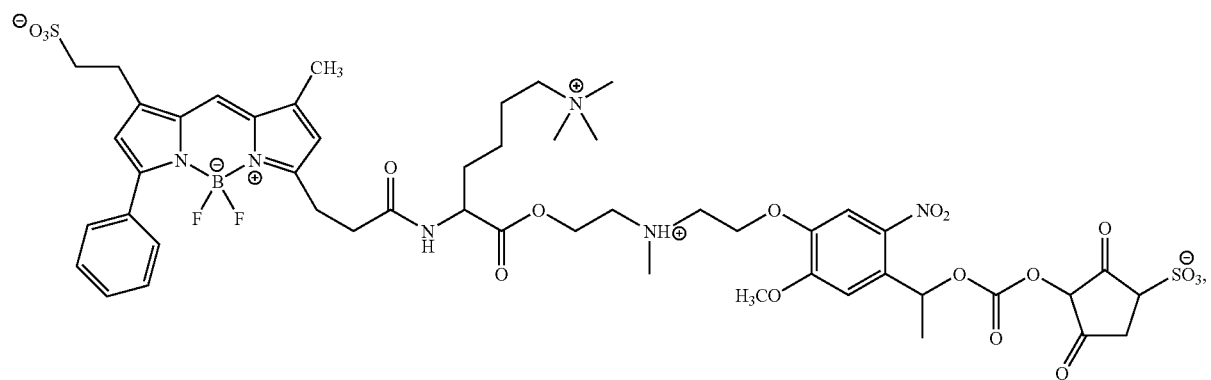

-continued
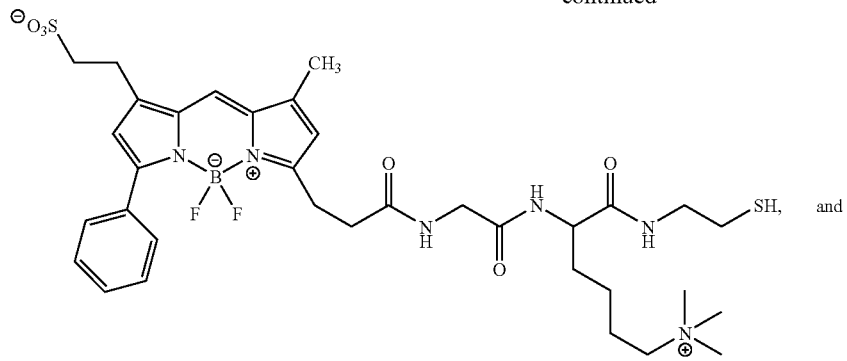
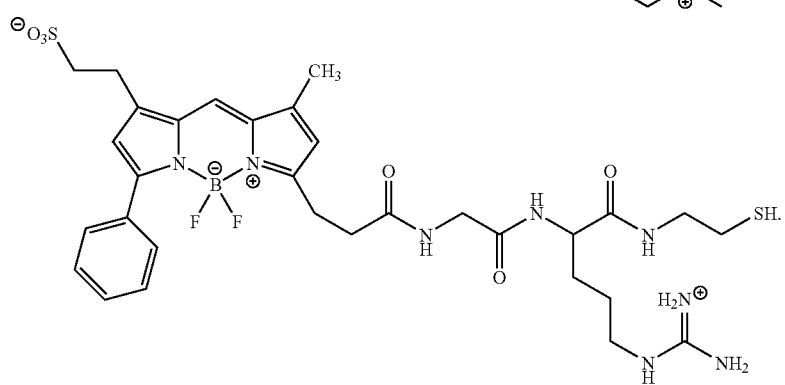
* * * * *

UNITED STATES PATENT AND TRADEMARK OFFICE
CERTIFICATE OF CORRECTION

| | | |
|---|---|---|
| PATENT NO. | : 7,582,260 B2 | Page 1 of 1 |
| APPLICATION NO. | : 10/761818 | |
| DATED | : September 1, 2009 | |
| INVENTOR(S) | : Dratz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1200 days.

Signed and Sealed this

Third Day of May, 2011

David J. Kappos
*Director of the United States Patent and Trademark Office*